United States Patent
Walker et al.

(10) Patent No.: US 10,143,526 B2
(45) Date of Patent: Dec. 4, 2018

(54) ROBOT-ASSISTED DRIVING SYSTEMS AND METHODS

(71) Applicant: Auris Health, Inc., Redwood City, CA (US)

(72) Inventors: Sean Walker, Fremont, CA (US); Curtis Caton, San Jose, CA (US); Terence Welsh, Mountain View, CA (US); Neha Virmani, Mountain View, CA (US); Yu Chiu, Mountain View, CA (US); June Park, Palo Alto, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 15/365,230

(22) Filed: Nov. 30, 2016

(65) Prior Publication Data

US 2017/0151027 A1    Jun. 1, 2017

Related U.S. Application Data

(60) Provisional application No. 62/261,301, filed on Nov. 30, 2015, provisional application No. 62/304,051, filed on Mar. 4, 2016.

(51) Int. Cl.
*G06K 9/00* (2006.01)
*A61B 34/37* (2016.01)
(Continued)

(52) U.S. Cl.
CPC .............. *A61B 34/37* (2016.02); *A61B 5/066* (2013.01); *A61B 6/504* (2013.01); *A61B 34/20* (2016.02);
(Continued)

(58) Field of Classification Search
USPC ........................................................ 382/128
See application file for complete search history.

(56) References Cited

U.S. PATENT DOCUMENTS

| | | | |
|---|---|---|---|
| 4,748,969 | A | 6/1988 | Wardle |
| 5,408,263 | A | 4/1995 | Kikuchi |

(Continued)

FOREIGN PATENT DOCUMENTS

| | | |
|---|---|---|
| DE | 102013100605 | 7/2014 |
| EP | 1 566 150 | 8/2005 |

(Continued)

OTHER PUBLICATIONS

Kukuk, Oct. 5, 2001, TBNA-protocols: Guiding TransBronchial Needle Aspirations Without a Computer in the Operating Room, MICCAI 2001, 2208:997-1006.

(Continued)

*Primary Examiner* — Jerome Grant, II
(74) *Attorney, Agent, or Firm* — Knobbe Martens Olson & Bear LLP

(57) ABSTRACT

Systems and methods for driving a flexible medical instrument to a target in an anatomical space with robotic assistance are described herein. The flexible instrument may have a tracking sensor embedded therein. An associated robotic control system may be provided, which is configured to register the flexible instrument to an anatomical image using data from the tracking sensor and identify one or more movements suitable for navigating the instrument towards an identified target. In some embodiments, the robotic control system drives or assists in driving the flexible instrument to the target.

20 Claims, 21 Drawing Sheets

(51) Int. Cl.
*A61B 6/00* (2006.01)
*A61B 5/06* (2006.01)
*A61B 5/055* (2006.01)
*A61B 6/03* (2006.01)
*A61B 34/10* (2016.01)
*A61B 34/30* (2016.01)
*A61B 34/20* (2016.01)
*A61B 90/00* (2016.01)
*A61B 5/00* (2006.01)

(52) U.S. Cl.
CPC .............. *A61B 34/30* (2016.02); *A61B 5/055* (2013.01); *A61B 5/7425* (2013.01); *A61B 6/032* (2013.01); *A61B 2034/107* (2016.02); *A61B 2034/2051* (2016.02); *A61B 2034/2061* (2016.02); *A61B 2034/301* (2016.02); *A61B 2090/365* (2016.02); *A61B 2090/374* (2016.02); *A61B 2090/376* (2016.02); *A61B 2090/3762* (2016.02)

(56) References Cited

U.S. PATENT DOCUMENTS

| | | | |
|---|---|---|---|
| 5,672,877 A * | 9/1997 | Liebig | A61B 6/5235 250/363.04 |
| 6,198,974 B1 | 3/2001 | Webster, Jr. | |
| 6,459,926 B1 | 10/2002 | Nowlin | |
| 6,837,846 B2 | 1/2005 | Jaffe | |
| 7,197,354 B2 * | 3/2007 | Sobe | A61B 5/06 600/407 |
| 7,772,541 B2 * | 8/2010 | Froggatt | G01M 11/083 250/226 |
| 8,442,618 B2 * | 5/2013 | Strommer | A61B 5/062 600/424 |
| 8,720,448 B2 | 5/2014 | Reis et al. | |
| 8,827,948 B2 * | 9/2014 | Romo | A61B 6/12 604/95.04 |
| 8,929,631 B2 * | 1/2015 | Pfister | A61B 6/487 382/130 |
| 8,945,095 B2 | 2/2015 | Blumenkranz | |
| 9,014,851 B2 * | 4/2015 | Wong | A61B 17/00 600/104 |
| 9,057,600 B2 | 6/2015 | Walker et al. | |
| 9,129,417 B2 * | 9/2015 | Zheng | G06T 7/66 |
| 9,226,796 B2 | 1/2016 | Bowling | |
| 9,256,940 B2 * | 2/2016 | Carelsen | G06T 7/73 |
| 9,271,663 B2 | 3/2016 | Walker et al. | |
| 9,283,046 B2 | 3/2016 | Walker et al. | |
| 9,289,578 B2 | 3/2016 | Walker et al. | |
| 9,314,306 B2 | 4/2016 | Yu | |
| 9,498,291 B2 | 11/2016 | Balaji et al. | |
| 9,504,604 B2 | 11/2016 | Alvarez | |
| 9,532,840 B2 | 1/2017 | Wong et al. | |
| 9,561,083 B2 | 2/2017 | Yu et al. | |
| 9,566,414 B2 | 2/2017 | Wong et al. | |
| 9,622,827 B2 | 4/2017 | Yu et al. | |
| 9,629,595 B2 | 4/2017 | Walker et al. | |
| 9,636,184 B2 | 5/2017 | Lee et al. | |
| 9,710,921 B2 | 7/2017 | Wong et al. | |
| 9,713,509 B2 | 7/2017 | Schuh et al. | |
| 9,727,963 B2 | 8/2017 | Mintz et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,827,061 B2 | 11/2017 | Balaji et al. | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 2003/0045778 A1 | 3/2003 | Ohline | |
| 2003/0182091 A1 | 9/2003 | Kukuk | |
| 2004/0257021 A1 | 12/2004 | Chang et al. | |
| 2005/0043718 A1 | 2/2005 | Madhani | |
| 2005/0065400 A1 | 3/2005 | Banik | |
| 2005/0256398 A1 | 11/2005 | Hastings | |
| 2005/0261551 A1 | 11/2005 | Couvillon | |
| 2006/0015096 A1 | 1/2006 | Hauck et al. | |
| 2006/0041293 A1 | 2/2006 | Mehdizadeh | |
| 2007/0013336 A1 | 1/2007 | Nowlin et al. | |
| 2007/0043455 A1 | 2/2007 | Viswanathan | |
| 2007/0135886 A1 | 6/2007 | Maschke | |
| 2007/0150155 A1 | 6/2007 | Kawai | |
| 2007/0249911 A1 * | 10/2007 | Simon | G06Q 50/24 600/300 |
| 2007/0253599 A1 | 11/2007 | White et al. | |
| 2007/0287992 A1 | 12/2007 | Diolaiti | |
| 2007/0299353 A1 * | 12/2007 | Harlev | A61B 5/0422 600/509 |
| 2008/0123921 A1 * | 5/2008 | Gielen | A61B 5/1127 382/131 |
| 2008/0231221 A1 | 9/2008 | Ogawa | |
| 2008/0255505 A1 | 10/2008 | Carlson et al. | |
| 2009/0076534 A1 | 3/2009 | Shelton | |
| 2009/0184825 A1 * | 7/2009 | Anderson | G06Q 10/087 340/572.1 |
| 2009/0198298 A1 * | 8/2009 | Kaiser | A61B 5/1104 607/17 |
| 2009/0245600 A1 | 10/2009 | Hoffman | |
| 2009/0287354 A1 | 11/2009 | Choi | |
| 2010/0030115 A1 | 2/2010 | Fujimoto | |
| 2010/0076263 A1 | 3/2010 | Tanaka | |
| 2010/0121138 A1 | 5/2010 | Goldenberg et al. | |
| 2010/0234856 A1 | 9/2010 | Stoianovici et al. | |
| 2010/0256812 A1 | 10/2010 | Tsusaka et al. | |
| 2011/0082462 A1 | 4/2011 | Suarez | |
| 2011/0137122 A1 | 6/2011 | Kawai | |
| 2011/0153252 A1 | 6/2011 | Govari | |
| 2011/0160570 A1 | 6/2011 | Kariv | |
| 2011/0319910 A1 | 12/2011 | Roelle et al. | |
| 2012/0046522 A1 | 2/2012 | Naito | |
| 2012/0071752 A1 | 3/2012 | Sewell | |
| 2012/0123441 A1 | 5/2012 | Au | |
| 2012/0209293 A1 | 8/2012 | Carlson | |
| 2012/0215094 A1 * | 8/2012 | Rahimian | A61B 1/00193 600/414 |
| 2012/0253276 A1 | 10/2012 | Govari et al. | |
| 2013/0090530 A1 | 4/2013 | Ramamurthy | |
| 2013/0102846 A1 | 4/2013 | Sjostrom | |
| 2013/0131503 A1 * | 5/2013 | Schneider | A61B 5/066 600/424 |
| 2013/0165945 A9 | 6/2013 | Roelle | |
| 2013/0325030 A1 | 12/2013 | Hourtash et al. | |
| 2014/0114180 A1 | 4/2014 | Jain | |
| 2014/0135985 A1 | 5/2014 | Coste-Maniere et al. | |
| 2014/0142591 A1 | 5/2014 | Alvarez et al. | |
| 2014/0163664 A1 | 6/2014 | Goldsmith | |
| 2014/0222207 A1 | 8/2014 | Bowling et al. | |
| 2014/0257334 A1 | 9/2014 | Wong et al. | |
| 2014/0264081 A1 | 9/2014 | Walker et al. | |
| 2014/0275985 A1 | 9/2014 | Walker et al. | |
| 2014/0275988 A1 | 9/2014 | Walker et al. | |
| 2014/0276392 A1 | 9/2014 | Wong et al. | |
| 2014/0276394 A1 | 9/2014 | Wong et al. | |
| 2014/0276646 A1 | 9/2014 | Wong et al. | |
| 2014/0276934 A1 | 9/2014 | Balaji et al. | |
| 2014/0276937 A1 | 9/2014 | Wong et al. | |
| 2014/0276938 A1 | 9/2014 | Hsu et al. | |
| 2014/0277747 A1 | 9/2014 | Walker et al. | |
| 2014/0296870 A1 | 10/2014 | Stern et al. | |
| 2014/0309649 A1 | 10/2014 | Alvarez et al. | |
| 2014/0316420 A1 * | 10/2014 | Ballard | A61B 17/7002 606/102 |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |

(56) References Cited

U.S. PATENT DOCUMENTS

| | | |
|---|---|---|
| 2015/0051592 A1 | 2/2015 | Kintz |
| 2015/0088161 A1 | 3/2015 | Hata |
| 2015/0101442 A1 | 4/2015 | Romo |
| 2015/0104284 A1 | 4/2015 | Riedel |
| 2015/0119628 A1* | 4/2015 | Bharat ................. A61N 5/1027 600/7 |
| 2015/0119638 A1 | 4/2015 | Yu et al. |
| 2015/0142013 A1 | 5/2015 | Tanner et al. |
| 2015/0164594 A1 | 6/2015 | Romo et al. |
| 2015/0164596 A1 | 6/2015 | Romo |
| 2015/0202015 A1 | 7/2015 | Elhawary |
| 2015/0223902 A1* | 8/2015 | Walker ............. A61B 17/12118 600/424 |
| 2015/0265359 A1 | 9/2015 | Camarillo |
| 2015/0265807 A1 | 9/2015 | Park et al. |
| 2015/0297864 A1 | 10/2015 | Kokish et al. |
| 2015/0314110 A1 | 11/2015 | Park |
| 2015/0335480 A1 | 11/2015 | Alvarez et al. |
| 2015/0342695 A1 | 12/2015 | He |
| 2015/0359597 A1 | 12/2015 | Gombert et al. |
| 2015/0374956 A1 | 12/2015 | Bogusky |
| 2015/0375399 A1 | 12/2015 | Chiu et al. |
| 2016/0001038 A1 | 1/2016 | Romo et al. |
| 2016/0005168 A1* | 1/2016 | Merlet ................ G06T 19/003 382/131 |
| 2016/0016319 A1 | 1/2016 | Remirez |
| 2016/0045269 A1* | 2/2016 | Elhawary ............... A61B 17/34 606/130 |
| 2016/0051221 A1* | 2/2016 | Dickhans ............. A61B 8/0841 600/424 |
| 2016/0066794 A1* | 3/2016 | Klinder ................. A61B 5/026 600/424 |
| 2016/0081568 A1 | 3/2016 | Kolberg |
| 2016/0100772 A1 | 4/2016 | Ikuma |
| 2016/0175059 A1 | 6/2016 | Walker et al. |
| 2016/0202053 A1 | 7/2016 | Walker et al. |
| 2016/0213884 A1 | 7/2016 | Park |
| 2016/0228032 A1* | 8/2016 | Walker ................. A61B 5/061 |
| 2016/0270865 A1 | 9/2016 | Landey et al. |
| 2016/0278865 A1* | 9/2016 | Capote ................. A61B 19/54 |
| 2016/0287111 A1* | 10/2016 | Jacobsen ............... A61B 5/002 |
| 2016/0287279 A1 | 10/2016 | Bovay et al. |
| 2016/0296294 A1 | 10/2016 | Moll et al. |
| 2016/0331469 A1* | 11/2016 | Hall ..................... A61B 5/066 |
| 2016/0338787 A1 | 11/2016 | Popovic |
| 2016/0346924 A1 | 12/2016 | Hasegawa |
| 2016/0354057 A1* | 12/2016 | Hansen ............... A61B 8/0841 |
| 2016/0360949 A1 | 12/2016 | Hyodo |
| 2016/0374541 A1 | 12/2016 | Agrawal et al. |
| 2017/0007337 A1 | 1/2017 | Dan |
| 2017/0056215 A1* | 3/2017 | Nagesh .................. A61F 2/856 |
| 2017/0065356 A1 | 3/2017 | Balaji et al. |
| 2017/0065364 A1 | 3/2017 | Schuh et al. |
| 2017/0065365 A1 | 3/2017 | Schuh |
| 2017/0068796 A1* | 3/2017 | Passerini ............. G06F 17/5009 |
| 2017/0100084 A1 | 4/2017 | Walker et al. |
| 2017/0100199 A1 | 4/2017 | Yu et al. |
| 2017/0105803 A1 | 4/2017 | Wong et al. |
| 2017/0113019 A1 | 4/2017 | Wong et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0165503 A1* | 6/2017 | Hautvast ............. A61N 5/1048 |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0209224 A1 | 7/2017 | Walker et al. |
| 2017/0251988 A1* | 9/2017 | Weber ...................... A61B 6/12 |
| 2017/0280978 A1 | 10/2017 | Yamamoto |
| 2017/0281049 A1 | 10/2017 | Yamamoto |
| 2017/0290631 A1 | 10/2017 | Lee et al. |
| 2017/0304015 A1* | 10/2017 | Tavallaei ............... A61B 34/35 |
| 2017/0325715 A1* | 11/2017 | Mehendale ........... A61B 5/062 |
| 2017/0333679 A1 | 11/2017 | Jiang |
| 2017/0340396 A1 | 11/2017 | Romo et al. |
| 2017/0360418 A1 | 12/2017 | Wong et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0056044 A1 | 3/2018 | Choi et al. |

FOREIGN PATENT DOCUMENTS

| | | |
|---|---|---|
| EP | 2 392 435 | 12/2011 |
| EP | 3 025 630 | 6/2016 |
| WO | WO 01/56457 | 8/2001 |
| WO | WO 06/122061 | 11/2006 |
| WO | WO 09/120940 | 10/2009 |
| WO | WO 11/132409 | 10/2011 |

OTHER PUBLICATIONS

Verdaasdonk et al., Jan. 23, 2013, Effect of microsecond pulse length and tip shape on explosive bubble formation of 2.78 μm Er,Cr;YSGG and 2.94 μm Er:YAG laser, Proceedings of SPIE, vol. 8221, 12.

* cited by examiner

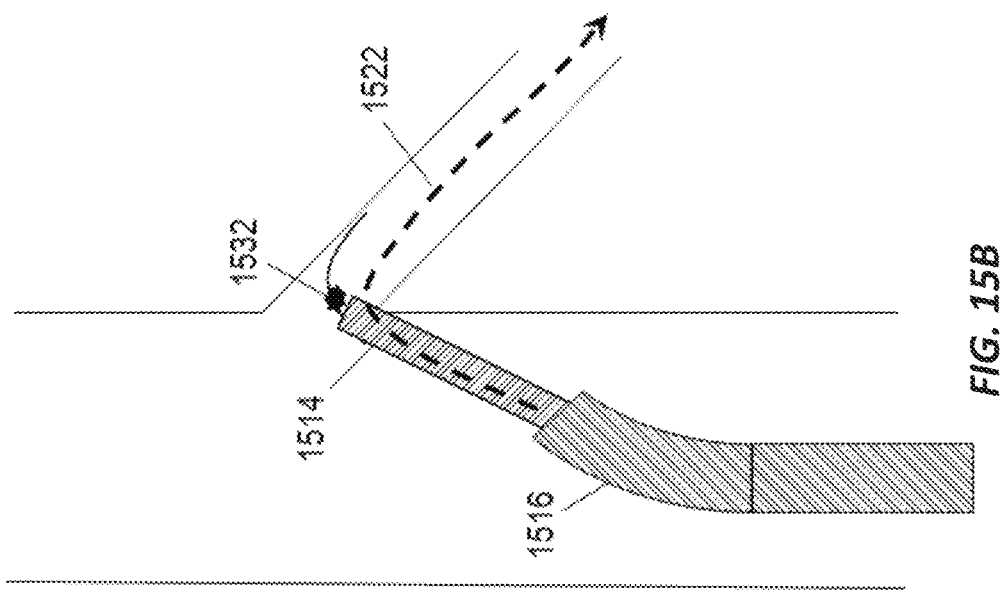
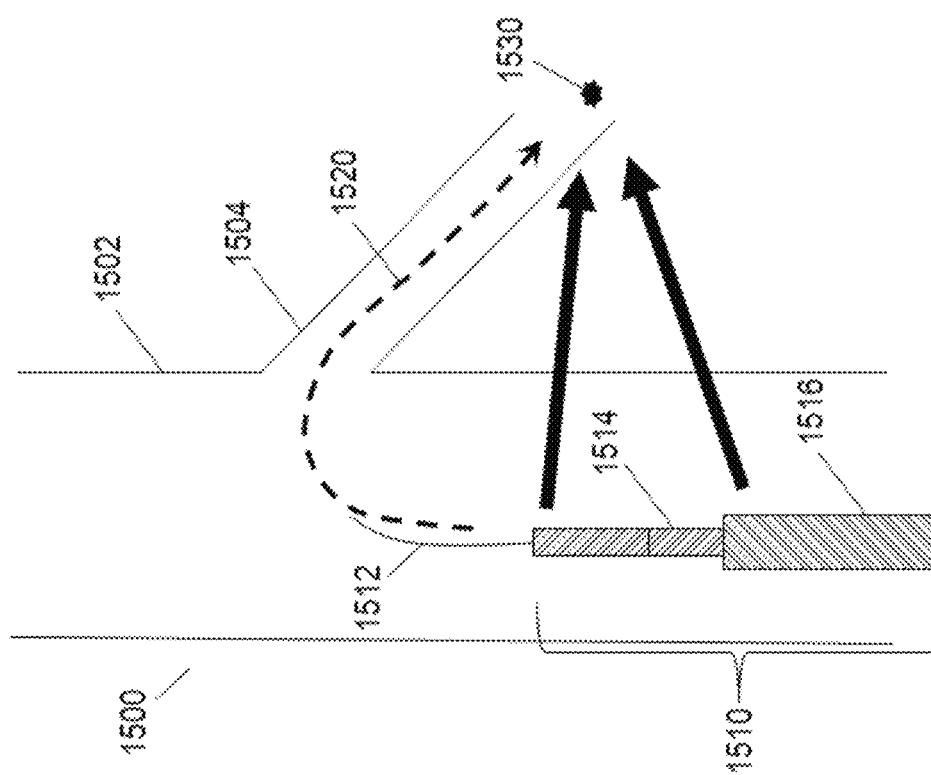
FIG. 15B
FIG. 15A

ROBOT-ASSISTED DRIVING SYSTEMS AND METHODS

CROSS-REFERENCE TO RELATED APPLICATIONS

This application claims the benefit under 35 U.S.C. § 119 to U.S. Provisional Application Nos. 62/261,301 filed Nov. 30, 2015, entitled "ROBOT-ASSISTED IMAGE-GUIDED NAVIGATION SYSTEMS AND METHODS," and 62/304,051, filed Mar. 4, 2016. The foregoing applications are hereby incorporated herein by reference in their entireties for all purposes.

INCORPORATION BY REFERENCE

All publications and patent applications mentioned in this specification are herein incorporated by reference as if each individual publication and patent application was specifically and individually indicated to be incorporated by reference in its entirety.

TECHNICAL FIELD

This disclosure relates generally to flexible medical instruments, and more particularly, to systems and methods for tracking and/or controlling the movement, location, position, orientation, or shape of one or more parts of a flexible medical instrument disposed within an anatomical structure.

BACKGROUND

Minimally invasive procedures are increasingly being used by medical practitioners to diagnose and treat medical conditions. Compared to open surgery, minimally invasive procedures involve smaller incision sizes, resulting in less injury to patients, improved recovery times, and reduced complications. A growing number of procedures are performed minimally-invasively using an access point (e.g., an incision) positioned remotely from the site of diagnosis or treatment. For example, increasingly, cardiovascular procedures such as aortic valve repairs and vascular stent implantations are performed by entering the patient's vasculature via a small incision in the femoral artery.

Robotic surgical systems are well suited for minimally invasive medical procedures, because they provide a highly controllable yet minimally sized system to facilitate instrument navigation to areas that may lie deep within a patient. The Magellan® robotic catheter system manufactured by Hansen Medical Inc. (Mountain View, Calif.) is one such robotic surgical system; it includes a telescoping catheter system formed of an inner elongate member and an outer elongate member. Both the inner and outer members have multi-directional articulation capabilities. Such a system is described, for example, in U.S. Pat. No. 8,827,948. To navigate the robotic catheter using the system, the system's interface requires a user to direct the catheter's movement in multiple degrees of freedom. The user must direct axial translation (i.e., insertion and/or retraction) as well as an articulation angle magnitude (i.e., the bend) and articulation angle direction (i.e., the roll or roll plane) of both the inner and outer members. The user must also direct translation of a guidewire. While users can handle instrument navigation relatively well when navigating in a constrained space such as a narrow blood vessel, it becomes much more challenging to navigate in an organ, an ostium of a branch vessel, or other relatively open three-dimensional space. Navigation in such an open area forces the user to understand the three-dimensional relationship of the instrument relative to the anatomical target and determine in which plane the instrument will bend.

This task is difficult, in part, because navigating an instrument through a lumen of the patient from a remote patient access point to the desired site of a procedure requires manipulating the instrument without a direct line of sight of the instrument. A tracking system may be used to help locate the desired site of the procedure and visualize the navigation of the instrument to the desired site of the procedure. Tracking systems allow the user to visualize a patient's internal anatomy and the location and/or orientation of the instrument within the patient's anatomy.

Many visualization systems are not suitable for continuous real-time tracking of instruments though. For example, some systems such as positron emission tomography (PET), X-ray computed tomography (CT), and magnetic resonance imaging (MM) produce and combine many cross-sectional images of an object to generate a computer-processed image; such an image capture process is slow and movement within the photographed field during the image capture process produces image artifacts that make such systems unsuitable for real-time tracking of moving instruments in a body. Additionally, some visualization systems such as X-ray CT and fluoroscopy emit potentially harmful ionizing radiation, and the duration of their use should be limited when possible. Direct endoscopic imaging (e.g., with an intraluminal camera) is suitable for predominantly empty lumens such as the gastrointestinal tract but is not suitable for blood-filled vasculature.

Tracking systems such as electromagnetic (EM) tracking systems and fiber optic tracking systems provide a promising form of real-time instrument tracking. EM sensing functions by placing an EM sensing coil (i.e., an EM sensor) in a fluctuating magnetic field. The fluctuating magnetic field induces a current in the coil based on the coil's position and orientation within the field. The coil's position and orientation can thus be determined by measuring the current in the coil. A single EM sensor is able to sense its position and orientation in three-dimensional space with five degrees of freedom (i.e., in every direction except roll). That is, the EM sensor is able to sense orientation in every direction except around the axial symmetric axis of the coil. Two EM sensors held fixed relative to each other on an instrument may be used to sense all six degrees of freedom of the instrument. In a navigation system employing EM tracking, an image of an anatomical space is acquired, the position and orientation of one or more EM sensors on an instrument are detected, and the system uses a registration between an EM sensor frame of reference and an anatomical space frame of reference to depict movement of the tracked instrument within the imaged anatomical space. The use of EM sensors to track medical instruments and localize them to a reference image is described, for example, in U.S. Pat. Nos. 7,197,354 and 8,442,618. Fiber optic position tracking or shape sensing devices are described, for example, in U.S. Pat. No. 7,772,541. In one example of fiber optic position tracking, a multi-core optical fiber is provided within a medical instrument, with a light source coupled to one end of the optical fiber and a detector coupled to the opposing end. The detector is configured to detect light signals that pass through the optical fiber, and an associated controller is configured to determine the geometric configuration of at least a portion of the medical instrument based on a spectral analysis of the reflected portions of the light signals. With such tracking systems, a medical practitioner can, in theory, observe movements of the instrument on a display and adjust user inputs as needed to navigate the instrument to a target location.

In practice, users often struggle to navigate instruments to target locations with existing tracking systems. One cause of the problem is that, for flexible instruments such as catheters, their shape inside the anatomy adjusts to the shape of the anatomy as the instrument is inserted. This shape does not always adjust uniformly or in a manner that is simple to predict, in part, because the stiffness of a flexible instrument is not uniform along the instrument. For example, in a telescoping catheter, a proximal segment of the outer member is stiffer than its articulation section, and the stiffness of the inner member increases if a guidewire is inserted inside. This lack of uniformity and predictability can be problematic when inserting a flexible instrument into an anatomy, especially when using a tracking system with sensors that only track discrete point(s) on the instrument (such as EM tracking sensors). With such systems, it can be difficult to discern the entire shape of the instrument.

Users also struggle to navigate instruments to target locations because robotic catheter systems are not always intuitive to drive. With flexible instruments that navigate through the anatomy, the instrument's tip position does not always follow the commanded position. This may be due to distortion from contact with the anatomy or deformation of the instrument due to articulation and insertion forces. This creates difficulty in knowing the actual position of the instrument. Tracking and localization make knowledge of the instrument position in three dimensions more visible to the user, but many medical practitioners still struggle to navigate the instrument to the desired anatomical target even when a live-tracked instrument is displayed over an image of the anatomy.

The struggle is largely due to the nature of the two-dimensional information being displayed to the practitioners. Some imaging systems have incorporated 2-D/3-D image fusion systems, for example, as described in U.S. Pat. No. 5,672,877. In one example, a fluoroscopic system can receive a pre-operative three-dimensional dataset from a CT or MRI and acquire two-dimensional images of the organ cavity or portion of the patient undergoing the interventional procedure. These systems can then generate a 3-D/2-D fusion visualization of the organ cavity or portion of the patient based on the acquired two-dimensional image and the three-dimensional image dataset. The three-dimensional image dataset is registered to the two-dimensional image. The three-dimensional image dataset and the two-dimensional image are then displayed as a 3-D/2-D fusion visualization, providing a 3-D model. However, even if a three-dimensional model is provided to help a user visualize the instrument in space, the instrument representation is ultimately projected onto a screen in two dimensions. Many users find it difficult to "think in three dimensions" (i.e., mentally convert two-dimensional images into the three-dimensional model).

Accordingly, there is a need for new and useful robotic systems that combine the capabilities of 3-D imaging and 3-D tracking while addressing the unique challenges of flexible instruments to assist users in navigating instruments within the human body.

SUMMARY

Various aspects of the present disclosure address one or more of the needs identified herein. For example, one aspect of the disclosure is directed to a method for driving a flexible medical instrument in three dimensional space within an anatomy. The method, performed by a robotic medical system, includes at least some of the following elements: acquiring one or more images pre-procedurally; acquiring one or more intra-procedure images; registering the intra-procedure images with the pre-procedure images so that image frames from the pre-procedure images are matched to those from the intra-procedure images; inserting a flexible medical instrument intraluminally into a patient, the instrument having one or more tracking sensors embedded therein; acquiring localization information for the instrument from the tracking sensors and tracking the location and position of at least a portion of the medical instrument using a tracking subsystem; superimposing the current location and position of at least a portion of the medical instrument on the registered images; identifying a target in the registered images; receiving a user command to drive the instrument; calculating a movement suitable to move the medical instrument from its current location to or towards the target; and navigating or assisting a user in navigating the medical instrument to the target based, at least in part, on the calculated movement.

In some embodiments, superimposing the current location and position of at least a portion of the medical instrument on the registered images includes overlaying a graphical representation of the instrument on at least two different images to depict the instrument relative to the anatomy in different viewing angles. In some embodiments, the target is identified within the registered images by the user. In some embodiments, the user provides the robotic medical system with an identification of the target using a user input device. In some embodiments, the user command to drive the instrument is received from the user via a user input device. In some embodiments, calculating a suitable movement includes calculating one or a series of bends, rolls, insertions, and/or retractions needed to move the instrument from its current location to or towards the target. In some embodiments, calculating the suitable movement includes determining a suitable change in instrument position in at least one degree of freedom. In some embodiments, receiving the user command includes receiving a user command to drive the instrument in a single two-dimensional plane, and calculating the suitable movement includes identifying a suitable rotation of the instrument in a third dimension. In some embodiments, navigating the medical instrument to the target location includes navigating a distal tip of a flexible inner member of the medical instrument to the target and driving a tubular outer member over the flexible inner member such that the tubular outer member generally follows over a path defined by the flexible inner member. In some embodiments, assisting the user in navigating the medical instrument to the target includes controlling movement of the medical instrument in at least one un-commanded degree of freedom while the user commands movement in one or more other degrees of freedom.

Another aspect of the present disclosure is directed to a method of driving a flexible instrument in three-dimensional space. The method includes: identifying a target location to which a user desires to drive a flexible instrument, the flexible instrument including a flexible inner member and a tubular outer member; navigating a distal tip of the flexible inner member to the target; and advancing the tubular outer member over the flexible inner member such that the tubular outer member follows over a path defined by the flexible inner member. The navigation of the distal tip of the flexible inner or outer member to the target may be performed automatically or in conjunction with user inputs. The navigation of some embodiments includes determining and commanding one or more instrument movements needed to navigate the flexible instrument to or towards the target location. An additional aspect of the disclosure is directed to a robotic medical system configured to perform such a method. In some embodiments, the system includes a user input device, an instrument driver, a controller in electrical communication with the user input device and the instrument driver, a tracking subsystem, and a medical instrument comprising a guidewire, a flexible inner member, and a tubular outer member. In some embodiments, the tracking subsystem includes position tracking sensors integrated into distal portions of the flexible inner member, the flexible outer member, and the guidewire. In some embodiments, the system further includes a display screen.

Another aspect of the present disclosure is directed to a robotic medical system for navigating a flexible instrument to a target anatomical location. The flexible instrument has at least one controllable bending section and at least one position tracking sensor coupled thereto. In various embodiments, the robotic medical system includes a user input device, an instrument driver, and a controller in electrical communication with the user input device and the instrument driver. The controller of some embodiments includes a processor and memory with instructions stored thereon, and the instructions, when executed, cause the controller to: obtain a target location; receive one or more user inputs from the user input device; and in response to a user input commanding a movement of the flexible instrument, determine and command movement of the flexible instrument in at least one degree of freedom in order to help direct the instrument toward the target location.

Another aspect of the disclosure is directed to a robotic medical system that includes a flexible instrument, a tracking subsystem, a user workstation, an instrument driver, and a controller. In various embodiments, the flexible instrument includes a proximal portion, a distal portion, and at least one controllable bending segment in the distal portion. The tracking subsystem of various embodiments includes at least one position tracking sensor integrated at the distal portion of the flexible instrument. The user workstation of various embodiments includes a user input device and a display screen. The instrument driver is operably coupled to the flexible instrument and includes motors and other hardware configured to insert and retract the flexible instrument and manipulate the at least one controllable bending segment. The controller of various embodiments is in electrical communication with the user workstation and the instrument driver. Moreover, the controller includes a processor and memory with instructions stored thereon, wherein the instructions, when executed, cause the controller to perform a method that includes: signaling the display screen to display an image of the flexible instrument over an image of an anatomical space, receiving an identification of a target location, determining one or more instrument movements needed to navigate the flexible instrument to or towards the target location, and sending commands to the instrument driver to thereby control navigation of the flexible instrument in the anatomical space in accordance with one or more user inputs received via the user input device and the one or more determined instrument movements. In some embodiments, the system further includes an imaging subsystem.

An additional aspect of the disclosure is directed to a method for controlling navigation of a flexible instrument navigable in three dimensional space. The method is performed by a robotic medical system that includes a flexible instrument, an imaging subsystem, a tracking subsystem having a tracking sensor integrated in the flexible instrument, an instrument driver, a workstation with a user input device and viewing screen, and a computer. In various embodiments, the method includes: acquiring an image with the imaging subsystem, acquiring localization information from the tracking sensor, registering the localization information to the image, overlaying the localization information on the image for display to the user, receiving an input from the user selecting a target on the image, and controlling navigation of the flexible instrument toward the target. In some embodiments, controlling navigation of the flexible instrument includes: receiving user inputs directing movement of the flexible instrument in a plane, directing movement of the flexible instrument in that plane based on the user inputs, and automatically determining and directing roll of the flexible instrument or movement in another plane.

A further aspect of the disclosure is directed to a method of providing navigation assistance to a user who is navigating a flexible instrument in an anatomical space of a patient. The method of various embodiments is performed by a computerized system and includes: acquiring and displaying at least two images of the anatomical space, each image displaying a different viewing angle; receiving a user designation of an anatomical target in each of the at least two images; calculating one or more movements required for the flexible instrument to move from a current position to or toward the anatomical target; and utilizing the calculated one or more movements to provide navigation assistance.

Additional exemplary configurations and advantages thereof will become apparent from the following detailed description and accompanying figures.

BRIEF DESCRIPTION OF THE DRAWINGS

FIGS. 10A-10C each provides two views as captured from a virtual biplane display while FIG. 10D provides a magnified view of one view from the virtual biplane display. Through the series of screen captures, FIGS.

10A-10D together illustrate one embodiment of a method performed by a robot-assisted instrument driving system.

Figure 11A:
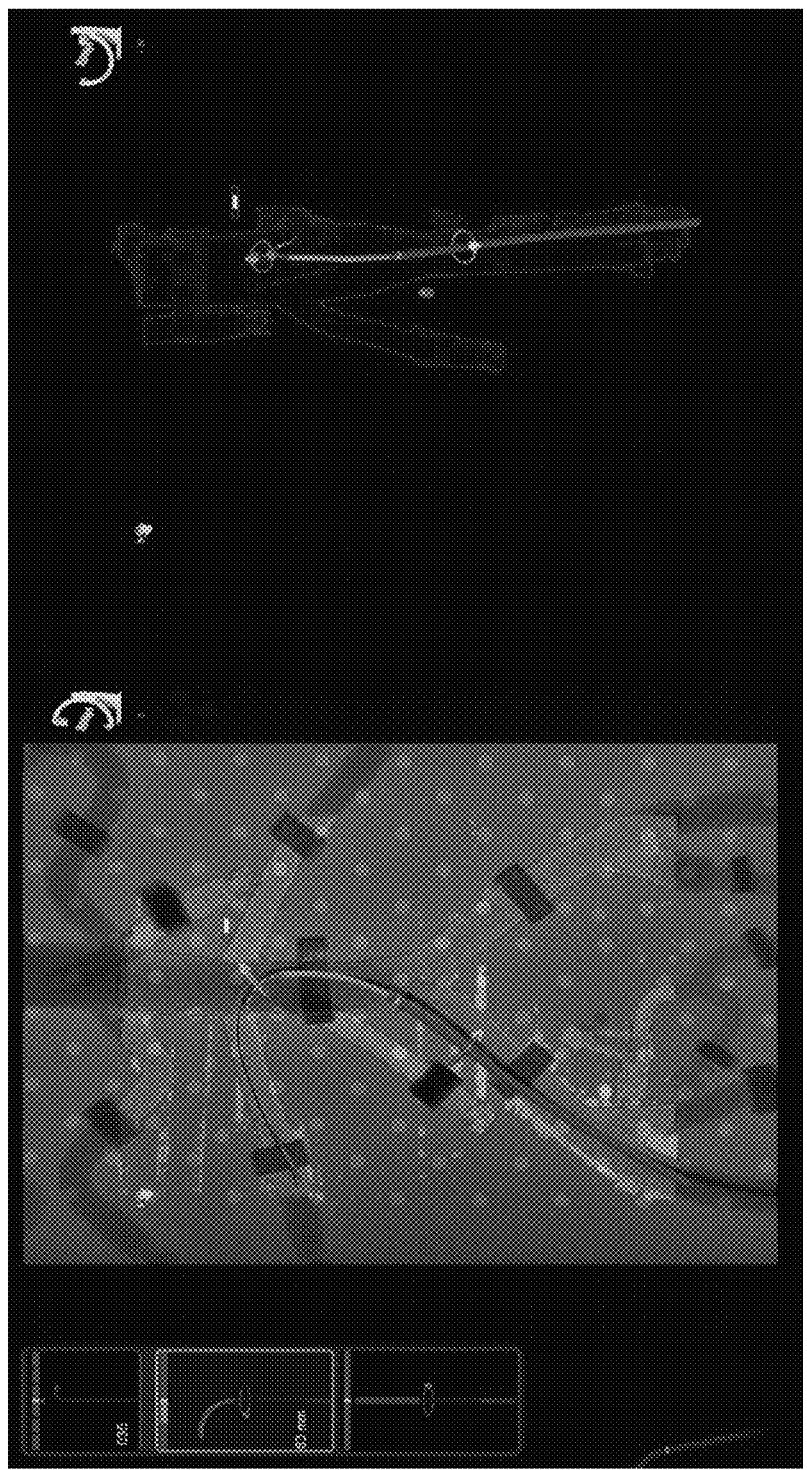
Figure 11B:
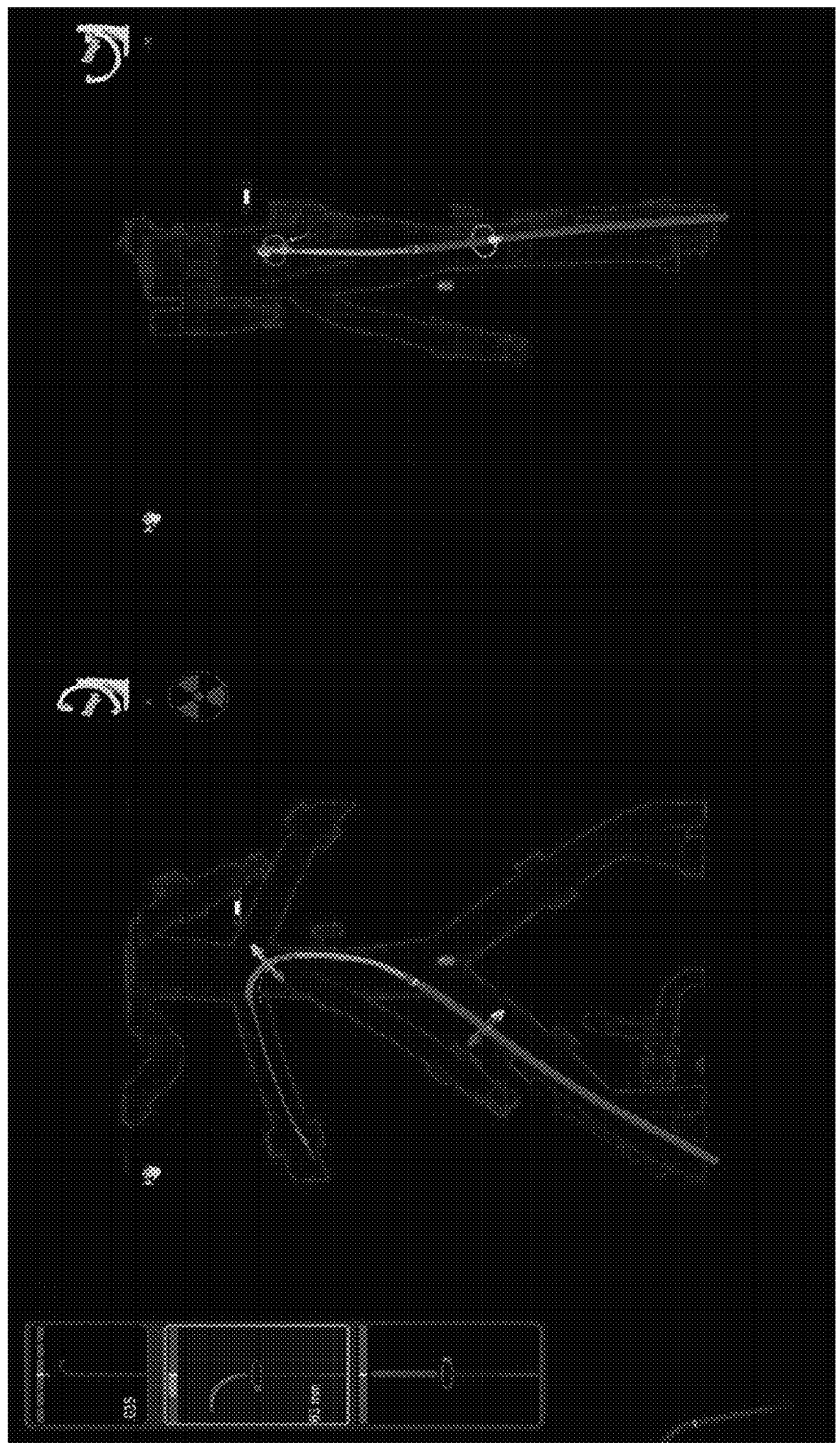

FIGS. 11A and 11B each illustrates a screen capture of one embodiment of a virtual biplane formed from two views of a segmented cone beam CT outline overlaid on either a fluoroscopy image or a plain background.

Figure 12B:
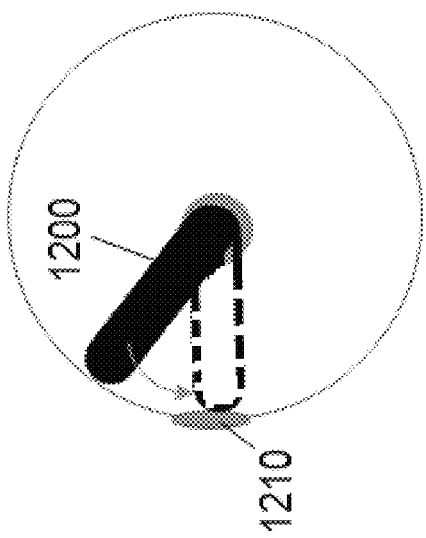
Figure 12A:
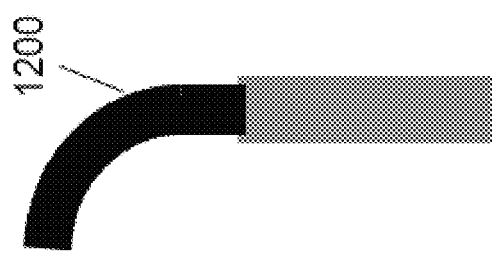

FIGS. 12A and 12B illustrate one embodiment of a virtual instrument from two different views: a side view and a front view, respectively. Both views may be provided within one embodiment of a virtual biplane.

Figure 13:
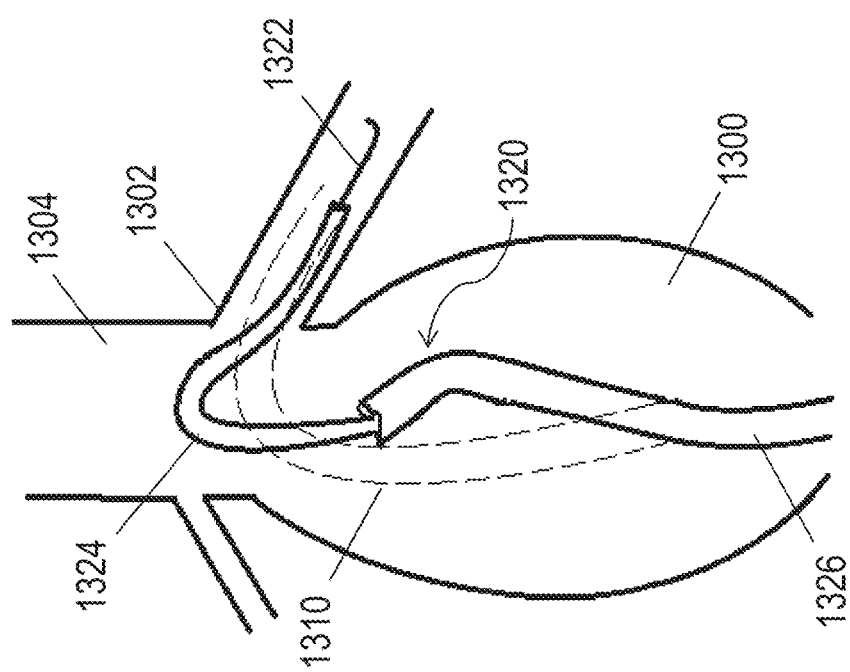

FIG. 13 illustrates one embodiment of an anatomical image with a virtual instrument superimposed thereon.

Figure 14:
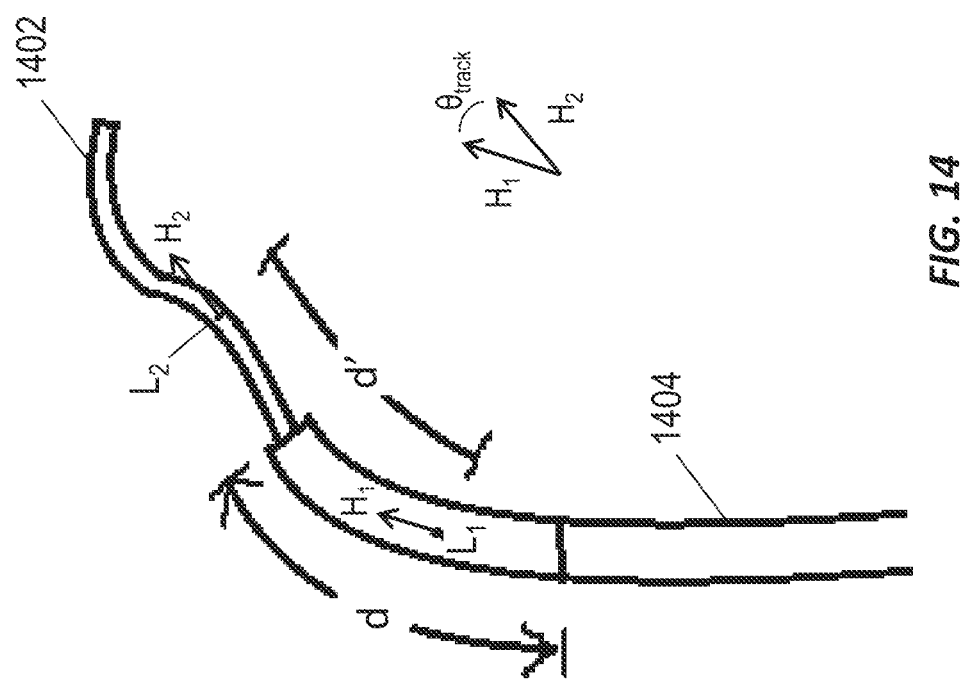

FIG. 14 illustrates a schematic representation of one embodiment of a virtual instrument along with various measurements of the virtual instrument acquired by one embodiment of a robot-assisted instrument driving system.

FIGS. 15A-15E illustrate one embodiment of an anatomical image with a virtual instrument superimposed thereon. Through the series of figures, FIGS. 15A-15E together illustrate one embodiment of a method of robot-assisted instrument driving.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the invention to these embodiments, but rather to enable any person skilled in the art to make and use this invention. Other embodiments may be utilized and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

Unless otherwise defined, each technical or scientific term used herein has the same meaning as commonly understood by one of ordinary skill in the art to which this disclosure belongs.

As used in the description and claims, the singular form "a", "an" and "the" include both singular and plural references unless the context clearly dictates otherwise. For example, the term "an EM sensor" may include, and is contemplated to include, a plurality of EM sensors. At times, the claims and disclosure may include terms such as "a plurality," "one or more," or "at least one;" however, the absence of such terms is not intended to mean, and should not be interpreted to mean, that a plurality is not conceived.

The term "about" or "approximately," when used before a numerical designation or range, indicates approximations which may vary by (+) or (−) 5%, 1% or 0.1%. All numerical ranges provided herein are inclusive of the stated start and end numbers. The term "substantially" indicates mostly (i.e., greater than 50%) or essentially all of a substance, feature, or element.

The terms "connected" and "coupled" are used herein to describe a relationship between two elements. The term "connected" indicates that the two elements are physically and directly joined to each other. The term "coupled" indicates that the two elements are physically linked, either directly or through one or more elements positioned therebetween. "Electrically coupled" or "communicatively coupled" indicates that two elements are in wired or wireless communication with one another such that signals can be transmitted and received between the elements.

As used herein, the term "comprising" or "comprises" is intended to mean that the device, system, or method includes the recited elements, and may additionally include any other elements. "Consisting essentially of" shall mean that the device, system, or method includes the recited elements and excludes other elements of essential significance to the combination for the stated purpose. Thus, a device, system, or method consisting essentially of the elements as defined herein would not exclude other elements that do not materially affect the basic and novel characteristic(s) of the claimed invention. "Consisting of" shall mean that the device, system, or method includes the recited elements and excludes anything more than trivial or inconsequential elements. Embodiments defined by each of these transitional terms are within the scope of this disclosure.

Figure 1:
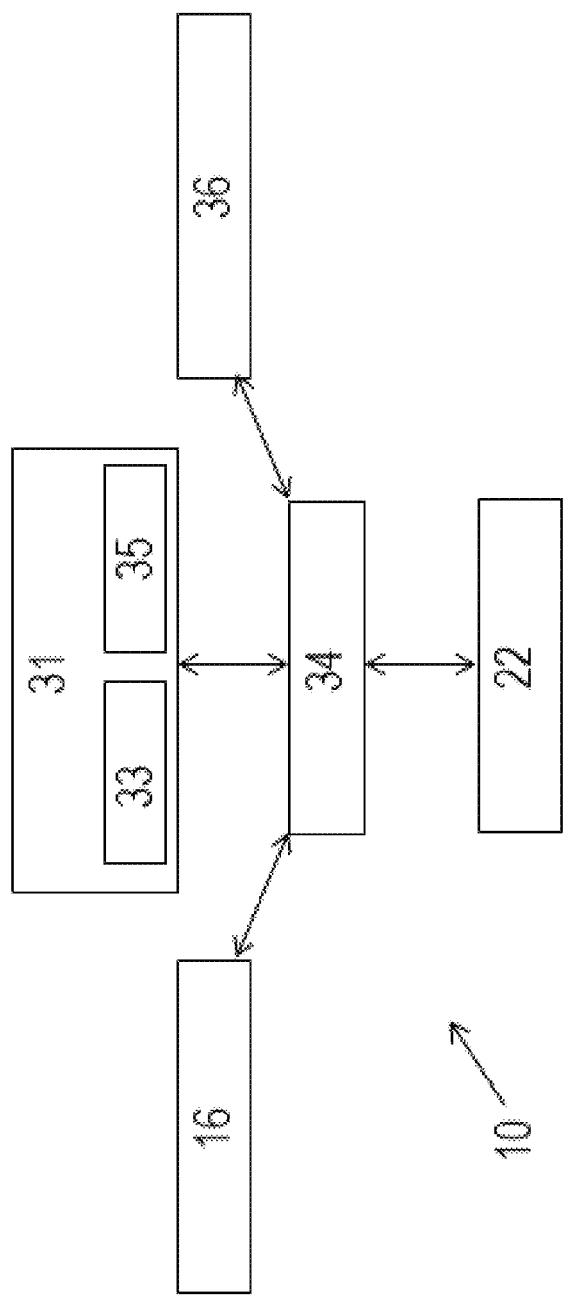
FIG. 1 illustrates a functional block diagram of one embodiment of a robot-assisted instrument driving system.

Disclosed herein are robot-assisted, image-guided instrument driving systems and methods for navigating a medical instrument through an anatomical three-dimensional space where no direct line of sight is available to a medical practitioner. As shown in FIG. 1, in various embodiments, the instrument driving system 10 includes an imaging subsystem 16, a tracking subsystem 36, a user workstation 31, an instrument driver 22, and a controller 34. Each of these elements and subsystems is discussed in detail below. With these elements and subsystems, the instrument driving system 10 is configured to assist in navigating a medical instrument 18 (not shown in FIG. 1) to a target location in a three-dimensional anatomical space.

In various embodiments, the medical instrument 18 is a flexible and/or elongate medical device or any other tool that may be inserted into a body lumen. As non-limiting examples, the instrument may be a catheter, sheath, leader, probe, biopsy needle, aspiration tool, endoscope, optical fiber, guidewire, tool for delivering or implanting a stent or valve, surgical tool, imaging tool, diagnostic tool, and/or therapeutic tool. In various embodiments, the medical instrument is robotically controlled. "Medical instrument," "elongate instrument," and "flexible instrument" are used interchangeably herein to refer generally to any robotically controlled instrument 18 configured for insertion into an anatomical lumen. In some embodiments, the medical instrument includes a flexible inner member and a tubular outer member. In some embodiments, the flexible inner member is a guidewire and the tubular outer member is a leader catheter. In other embodiments, the flexible inner member is a leader catheter and the tubular outer member is a sheath catheter. In still other embodiments, the flexible inner member is a guidewire and the tubular outer member is a sheath catheter. In some embodiments, a guidewire, leader catheter, and sheath catheter are provided.

In various embodiments, the elongate instruments 18 have one or more controllable bending sections or articulation sections. The bending sections are manipulatable to change the direction of the tip of the flexible instruments as they are being advanced into the patient. The deflection or bending of the tip is sometimes referred to as the "articulation angle" and the corresponding tip direction is sometimes referred to as the "heading direction". The bending section may be configured to bend directly in multiple planes relative to its non-articulated state, or it may be configured to first bend in one plane and be rotatable or rollable to reach another plane. The rotational orientation of the bending section is sometimes referred to as the "roll angle" or the "roll plane". In various embodiments, the elongate instrument 18 has a proximal portion and a distal portion. The terms "proximal"

and "distal" are relational terms defined from the frame of reference of a clinician or robot arm. The proximal portion is configured to be positioned closer to the clinician or robot arm and the distal portion is configured to be positioned closer to the patient or advanced further into the patient.

In various embodiments, the anatomical space is a three-dimensional portion of a patient's vasculature, tracheobronchial airways, urinary tract, gastrointestinal tract, or any organ or space accessed via such lumens. Images of the anatomical space may be acquired using any suitable imaging subsystem 16. Suitable imaging subsystems 16 include, for example, X-ray, fluoroscopy, CT, PET, PET-CT, CT angiography, Cone-Beam CT, 3DRA, single-photon emission computed tomography (SPECT), MRI, Optical Coherence Tomography (OCT), and ultrasound. One or both of pre-procedural and intra-procedural images may be acquired. In some embodiments, the pre-procedural and/or intra-procedural images are acquired using a C-arm fluoroscope, such as described in U.S. Pat. No. 8,929,631, the disclosure of which is herein incorporated by reference in its entirety. In the following discussion, the image and image acquiring device (i.e., the imager) are often referred to using the terms "fluoroscopy image" and "C-arm," respectively, but the invention is not limited to use with fluoroscopy images; the same techniques apply to a variety of imaging subsystems.

In various embodiments, the tracking subsystem 36 tracks the medical instrument 18 as the medical instrument 18 progresses through the anatomical space. As used herein, a tracking subsystem 36 may also be referred to as a position tracking system, a shape tracking system, or a localization subsystem. The term "localization" is used in the art in reference to systems and methods for determining and/or monitoring the position (i.e., location and/or orientation) of objects, such as medical instruments or tools in a reference coordinate system. Any suitable tracking system may be used. In many embodiments, the tracking subsystem 36 includes one or more sensors placed on or in the medical instrument 18 to enable tracking of the instrument 18. The tracking subsystem 36 further includes a computerized tracking device configured to detect the one or more sensors and/or receive data from the one or more sensors. In some embodiments provided herein, an electromagnetic (EM) sensing coil system is used. In other embodiments, a fiber optic tracking system or other tracking or localization system is used. The tracking sensor or localization sensor is often referred to herein as an EM sensor to avoid listing numerous sensors for each embodiment, but it should be emphasized that any tracking or localization sensor, including a fiber optic sensor, may be used.

A "sensed" medical instrument, as used at times herein, refers to an instrument that has a position tracking sensor embedded therein and is being tracked. A "localized" medical instrument, as used at times herein, refers to a sensed instrument that has been localized to a reference coordinate system. As described in more detail further below, in some embodiments, the reference coordinate system may be an image of the patient or a part of the patient anatomy.

Figure 2:
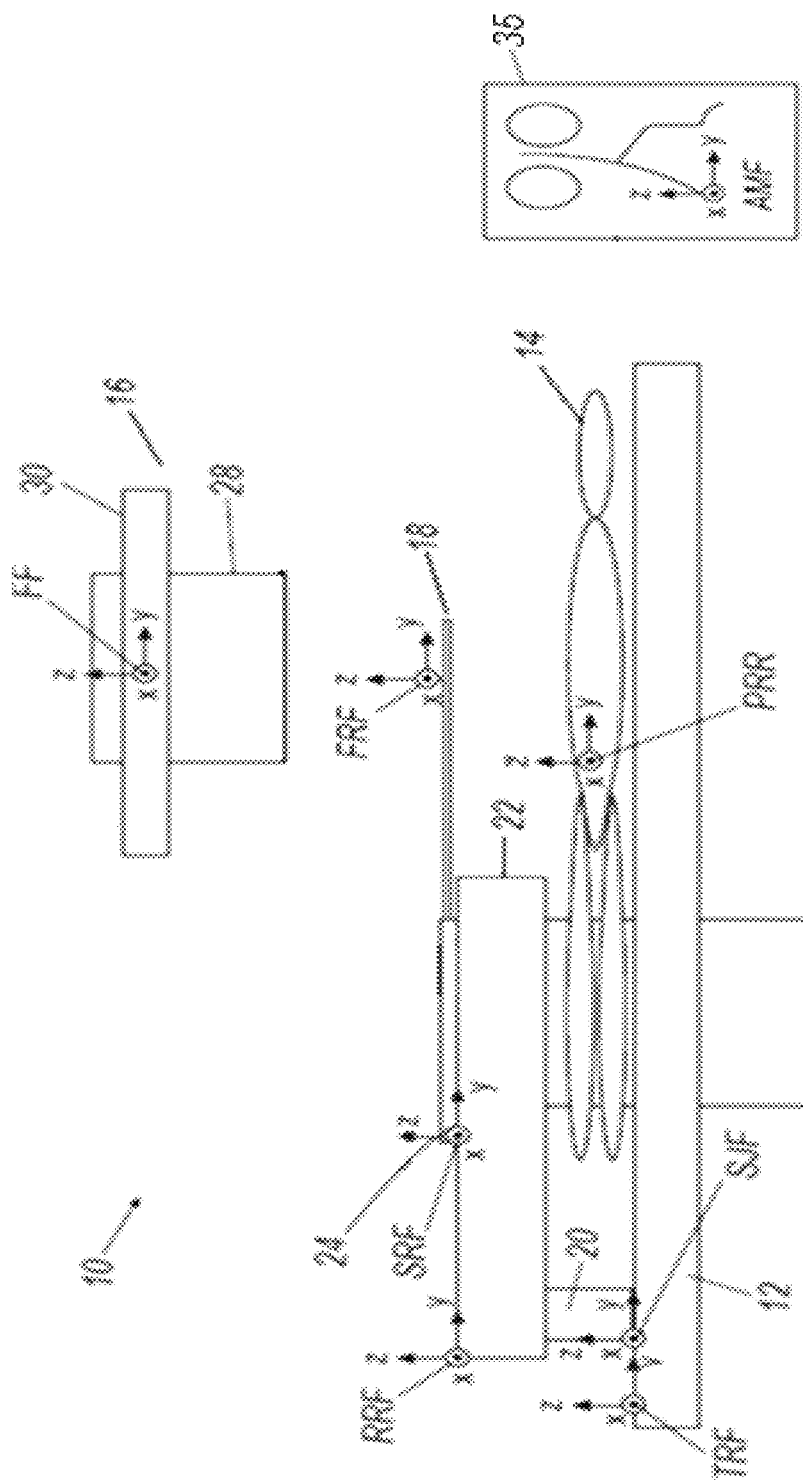
FIG. 2 illustrates a schematic representation of one embodiment of a robot-assisted instrument driving system provided within an operation room setup.

FIG. 2 provides one embodiment of an operating room setup that includes the robotically-assisted instrument driving system 10. The depicted system 10 includes a table 12 upon which a patient 14 may be placed, a fluoroscopy system or other imaging subsystem 16, and a catheter or other medical instrument 18. The depicted fluoroscopy system 16 includes a C-arm 28. A fluoroscopy panel 30 is mounted to the C-arm 28. The C-arm 28 is selectively moveable during the procedure to permit various images of the patient to be taken by the fluoroscopy panel 30.

Attached to the table 12 is a robotic arm (also referred to as a setup joint) 20 to which a robotic instrument driver 22 is coupled. One or more splayers 24 may be mounted to the instrument driver 22. In some embodiments, the splayers 24 are coupled to or form a portion of the medical instrument 18. The medical instrument 18 of some embodiments also includes one or more pullwires disposed therein. The pullwires are attached to an articulation section of the medical instrument 18 and extend along a length of the instrument 18 to a proximal end. In such embodiments, the splayers 24 are positioned at the proximal end of the instrument 18. Each of the splayers 24 may include a pulley about which one of the pullwires is wound and an interface for coupling with the robotic instrument driver 22. In some embodiments, the components are configured such that a motor in the robotic instrument driver 22 rotationally drives an output shaft, which rotates the pulley of the splayer 24 and thereby adjusts tension in the pullwire to articulate the articulation section of the medical instrument 18.

Figure 3:
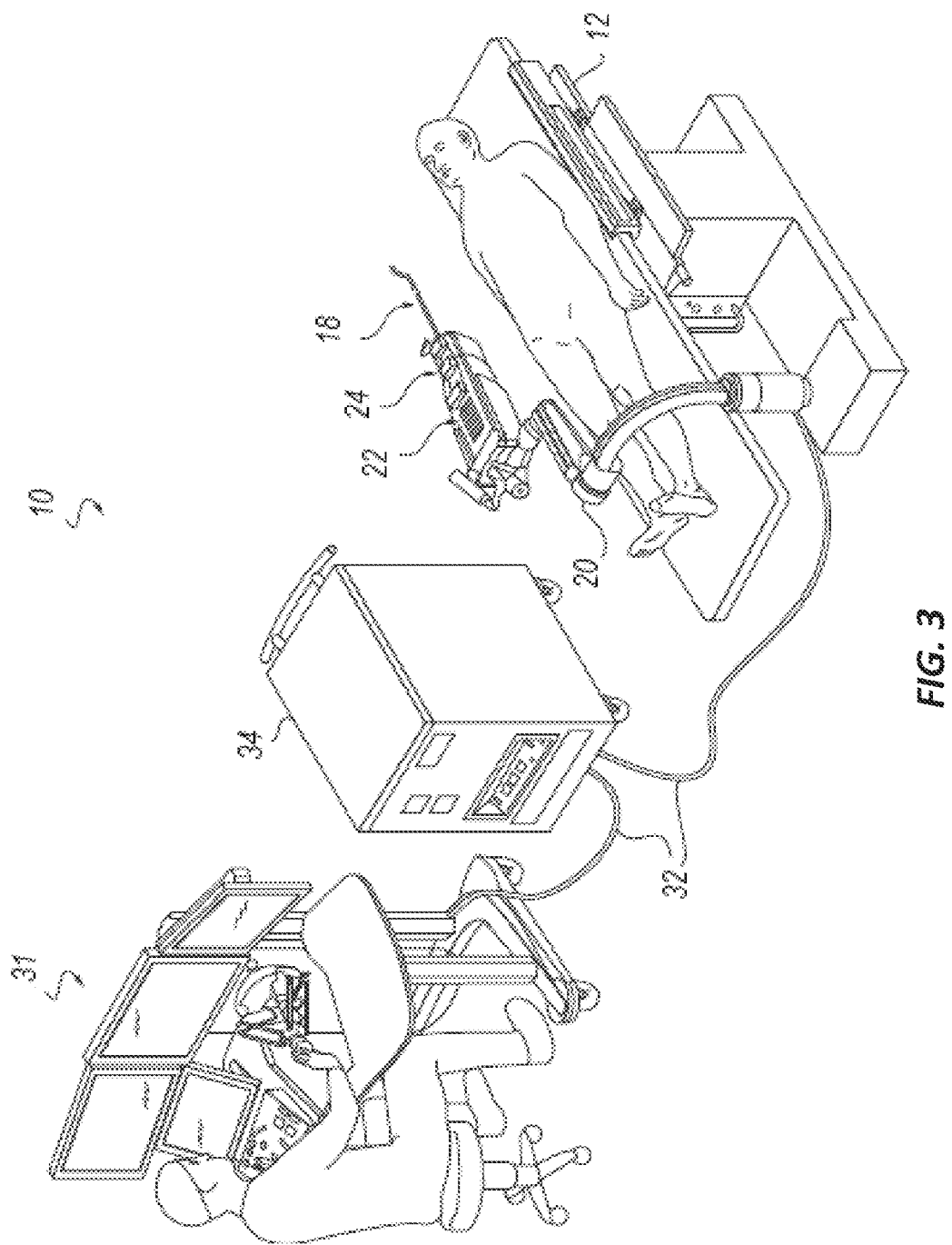
FIG. 3 illustrates a schematic representation of one embodiment of a robot-assisted instrument driving system.

The various components of the robotically-assisted instrument driving system 10 are further visible in FIG. 3. One or both of the user workstation 31 and the controller 34 may be remotely positioned (i.e., free of a physical connection) with respect to the table 12. In some embodiments, one or both of the user workstation 31 and the controller 34 are positioned in a separate room than the table 12. The user workstation 31 includes a computer, a control console having a user input device 33, and a visual display 35. The visual display 35 may be a touch screen, LCD screen, or any other suitable display configured to present one or more images to a user. The user input device 33 may include, but is not limited to, a multi-degree of freedom device having multiple joints and associated encoders. The user input device 33 may additionally or alternatively include a keyboard, joystick, buttons, switches, knobs, trackballs, touchscreen, or any other input devices suitable for receiving commands from, and interfacing with, a user.

Figure 4:
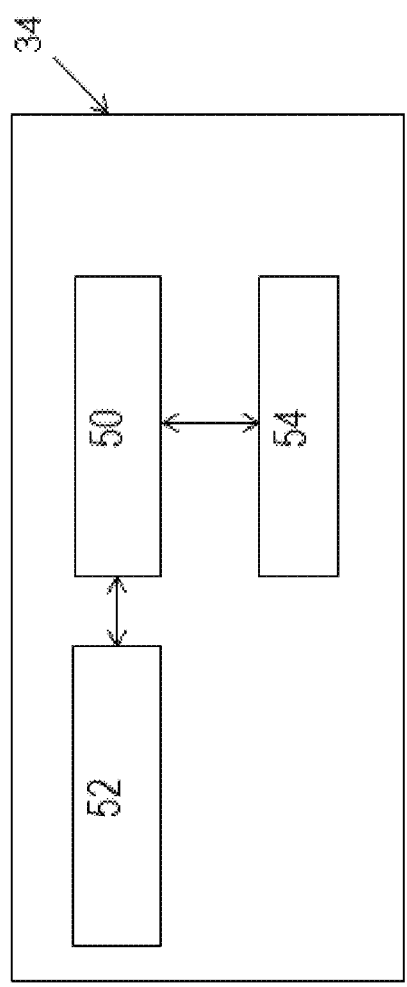
FIG. 4 illustrates a schematic block diagram of one embodiment of a controller for a robot-assisted instrument driving system.

The controller 34 is a computing device. As shown in FIG. 4, the controller 34 includes electronics, including a processor 50, and memory 52 having instructions stored thereon. The instructions, when executed by the processor 50, cause the processor 50 to perform various controls methods and execute various algorithms described elsewhere herein. The processor 50 may be a general purpose microprocessor, a digital signal processor (DSP), a field programmable gate array (FPGA), an application specific integrated circuit (ASIC), or other programmable logic device, or other discrete computer-executable components designed to perform the functions described herein. The processor 50 may also be formed of a combination of processing units, for example, a DSP and a microprocessor, a plurality of microprocessors, one or more microprocessors in conjunction with a DSP core, or any other suitable configuration.

The processor 50 is coupled, via one or more buses, to the memory 52 in order for the processor 50 to read information from and write information to the memory 52. The processor 50 may additionally or alternatively contain memory 52. The memory 52 can include, for example, processor cache. The memory 52 may be any suitable computer-readable medium that stores computer-readable instructions for execution by computer-executable components. For example, the computer-readable instructions may be stored on one or a combination of RAM, ROM, flash memory, EEPROM, hard disk drive, solid state drive, or any other suitable device. In various embodiments, the computer-readable instructions include application software stored in a non-transitory format. The software, when executed by the processor 50, causes the processor 50 to perform one or more operations described elsewhere herein.

The controller 34 further includes one or more interfaces 54 (e.g., communication databuses or network interfaces) for receiving user inputs from the user input device 33, transmitting images to the visual display 35, and transmitting commands to the robotic instrument driver 22. In some embodiments, the controller 34 is configured for bidirectional communication with the robotic instrument driver 22, enabling the controller 34 to receive torque data or other feedback from the instrument driver 22. In some embodiments, the controller 34 is physically coupled to the user input device 33 and/or visual display 35 of the user workstation 31. In some embodiments, the controller 34 is physically coupled to the robotic instrument driver 22. In other embodiments, the controller 34 is physically separate from, but communicatively coupled to the user workstation 31 and the robotic instrument driver 22 via a wireless connection. A communication link 32 transfers signals between the user workstation 31, the controller 34, and the robotic instrument driver 22. The communication link 32 may be a wired or wireless communication link.

Figure 5:
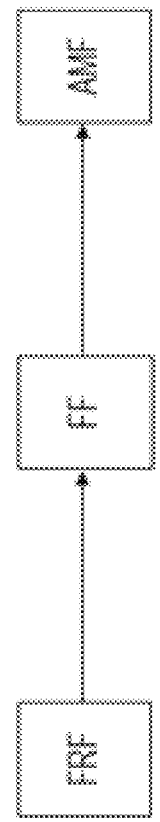
FIG. 5 illustrates a flow chart of one embodiment of a registration technique of correlating a sensor reference frame to other selective reference frames.

Each element of the robotic surgical system 10 positioned within the operating suite may define a separate reference frame to which localization sensors may be localized. More specifically, separate reference frames may be defined for each element of the robotic surgical system 10. Such reference frames may include, for example, the following shown in FIG. 2: a table reference frame TRF for the table 12, a setup joint reference frame SJF for the setup joint or arm 20, a robotic instrument driver reference frame RRF for the robotic instrument driver 22, a splayer reference frame SRF for the splayer 24, and a fluoroscopy reference frame FF for the fluoroscopy panel 30. Additional reference frames that may be defined in the system include: a patient reference frame PRR for the patient 14, a reference frame FRF for a tracking sensor disposed in or on the elongate instrument 18, and a pre-operative 3-D anatomical model reference frame AMF for the model depicted on the visual display 35. In various embodiments, the robotic surgical system 10 is designed to relate a coordinate system of the tracking sensor FRF of the elongate member 18 to either a fluoroscopy coordinate system FF or a pre-operative 3-D coordinate system AMF, as shown in FIG. 5. The robotic surgical system 10 may employ a variety of registration techniques to register the FRF to the FF or AMF, such as those described below or those described in U.S. Pat. No. 9,014,851 to Wong et al., the disclosure of which is herein incorporated by reference in its entirety.

In various embodiments, the position or shape tracking sensors incorporated into the medical instrument 18 allow for real-time sensing of the instrument's position (i.e., location, orientation, and/or shape). When the tracking sensor is integrated into the elongate instrument 18 and localized or registered to the anatomy or an image or model of the anatomy such that the position of the elongate instrument 18 is known relative to the anatomy, image, or model, a positionally-accurate representation of the instrument can be provided in the coordinate frame of the anatomical image or model. As the instrument 18 moves through the patient, the tracking information of the sensor can be used to update the position of the elongate instrument 18 relative to the anatomy, image, or model such that the representation of the elongate instrument can be displayed moving in real-time in an anatomical image or model. Additionally, with the instrument and the anatomical images provided in the same frame of reference, a target anatomy may be identified in multiple fluoroscopy views to localize the target's position in three dimensional (3-D) space relative to the elongate instrument. An aspect of the disclosure provided herein is to make use of this situation where the 3-D position of an instrument and a target are known in real-time relative to a user's view of the patient's anatomy in order to allow for novel navigation strategies not possible with traditional robotic or manual minimally-invasive instrument navigation. Robotic assisted driving, as provided herein, enhances the capabilities of an instrument control or tracking system by allowing a user to easily navigate the instrument through the complex anatomy to a target location without exposing the patient to excessive radiation during the procedure.

Figure 6:
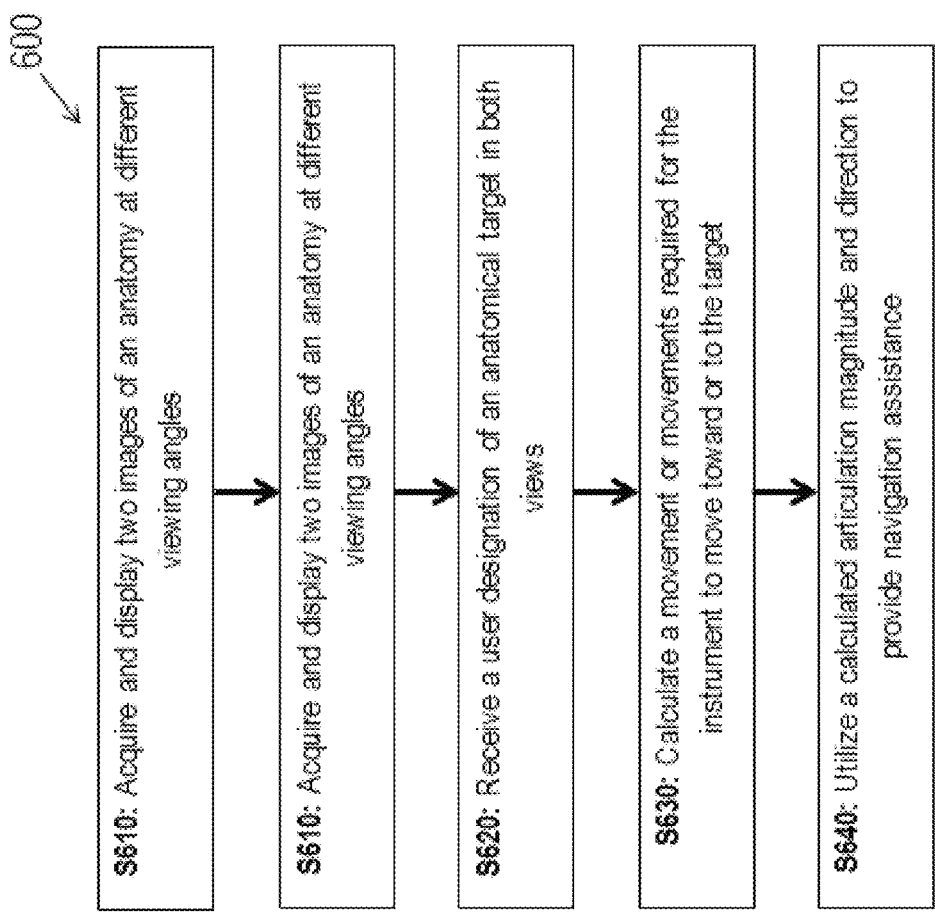
FIG. 6 illustrates a flow chart of one embodiment of a method of robotically assisting navigation of a medical instrument.

One method of performing robotic-assisted navigation is provided in FIG. 6. The method 600 is performed by a robotically-assisted instrument driving system, for example, the instrument driving system of FIGS. 1-4. In various embodiments, such a method 600 is performed by the robotically-assisted instrument driving system 10 in response to execution of the instructions stored in the memory 52 of the controller 34.

As shown in the depicted embodiment at S610, in some embodiments, the instrument driving system acquires and displays two images of a relevant anatomy at different viewing angles. The images are acquired by the imaging subsystem, and any suitable imaging modality may be used.

As shown at S620, in some embodiments, the system localizes and displays the position of an elongate medical instrument relative to the images of the patient's anatomy. In some embodiments, this step includes acquiring localization information for the instrument from a tracking sensor disposed in or on the instrument, tracking the position of at least a portion of the medical instrument using a tracking subsystem, correlating the position of the instrument to the patient's anatomy, and superimposing a positionally-accurate representation of the instrument on the two displayed images of the anatomy.

As shown at S630, in some embodiments, the system receives a user designation of an anatomical target in both images. The designation of the anatomical target in both images may be combined to compute a 3-D position (i.e., location, orientation, and/or shape) of an anatomical target.

As shown at S640, in some embodiments, the system calculates one movement or a series of movements required for the instrument to move from its current position toward, to, or through the target. This calculation can be done continuously as the instrument moves through the anatomy or on-demand after a specific event or action is taken by the user. In some embodiments, these calculations are computed for multiple instrument components simultaneously (for example, for an inner member and an outer member). In various embodiments, the calculated movements include one or more of a magnitude and direction of articulation (e.g., a bend and a roll). In some embodiments, the calculated movements further include one or more of a magnitude and direction of axial translation of one or more instrument components (e.g., the inner member).

As shown at S650, in some embodiments, the system utilizes the calculated movements to provide navigation assistance. The form of navigation assistance that is provided may vary widely between embodiments and/or modes. For example, the navigation assistance may include: providing step-by-step navigation instructions to the user, controlling navigation in one or more degrees of freedom, rejecting user-commanded movements that would navigate the instrument away from the target, driving the instrument towards the target while an auto-pilot indicator is actuated by the user, and/or driving the instrument to the target in a fully-automated manner.

Each element of the assisted-driving method and the components that make it possible are described in more detail below.

Tracking Sensors

In various embodiments, at least one tracking sensor is incorporated into the medical instrument to enable detection of the position (i.e., location, orientation, and/or shape) of the medical instrument. In some embodiments, at least one tracking sensor is integrated into a flexible inner member of a medical instrument; in some embodiments, at least one tracking sensor is additionally or alternatively integrated into a tubular outer member of the medical instrument. For example, in the embodiment of FIG. 7, EM sensors are incorporated into the various components of the elongate instrument 700. While numbered uniquely, one skilled in the art will appreciate that the medical instrument 18 of FIG. 1 may be formed of any embodiment of an instrument described herein and may include any of or all the features of the instrument 700 shown in FIG. 7. In the depicted embodiment, the medical instrument 700 includes an outer sheath catheter 710, an inner leader catheter 720, and a guidewire 730. The sheath catheter 710 and leader catheter 720 each have a flexible distal portion, referred to herein as the articulation section 716, 726, and a stiffer proximal portion, referred to herein as the shaft 712, 722. Two five-degree of freedom (DOF) sensors 714 are located at the base of the sheath articulation section 716, two 5-DOF sensors 724 are located at the base of the leader articulation section 726, and a single 5-DOF sensor 734 is located at or near the tip of the guidewire 730. The two EM sensors in each of the sheath and the leader form a pair of sensor coils in each instrument. These pairs of 5-DOF sensors enable tracking of each of the leader 720 and the sheath 710 in 6-DOF so that complete orientation, location, and heading are known. In the depicted embodiment of the guidewire 730, there is only enough space for a single 5-DOF sensor 734. In such embodiments, the guidewire position and direction are sensed, but not the roll.

Figure 8B:
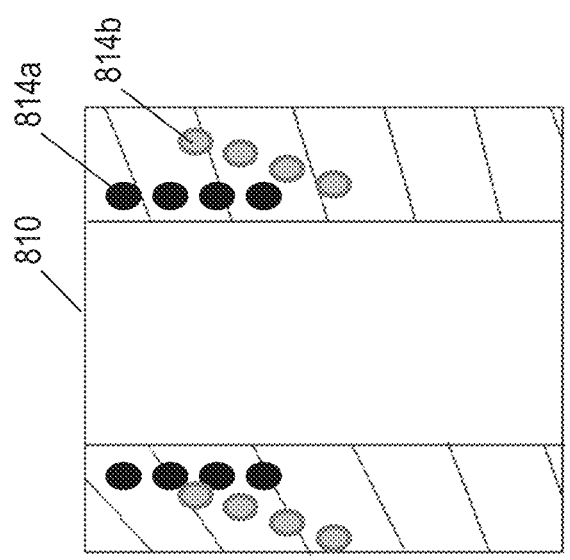
FIGS. 8A-8E illustrate schematic representations of some embodiments of tracking sensors, as positioned within a medical instrument.
Figure 8C:
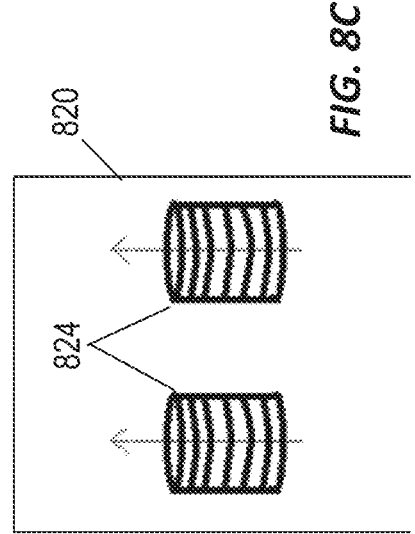
Figure 8A:
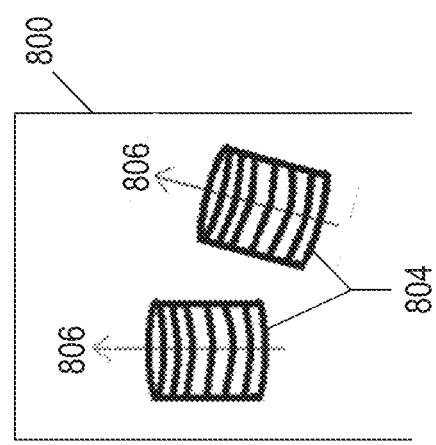
Figure 8D:
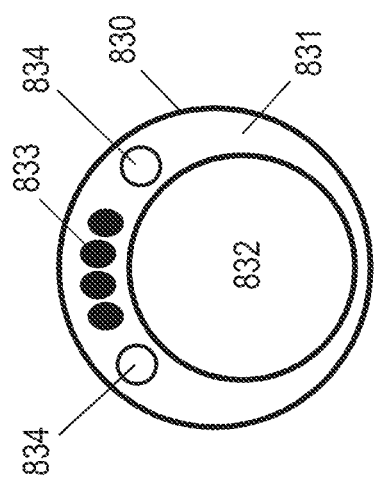

Combining two 5-DOF sensors into a single 6-DOF measurement (essentially calculating the roll angle of the instrument) can be accomplished in a number of ways. In one embodiment, two 5-DOF coils 804 are combined into a rigid assembly in a medical instrument 800 with known sensor locations and with the two coils 804 configured to have different orientations of their symmetric axes 806, as shown, for example, in FIG. 8A. This provides a strong or accurate 6-DOF measurement because the EM sensing technology is well-suited for sensing the heading, or symmetric axis, of the coils. There is, however, often inadequate space to place two nonparallel coils into an elongate instrument such as a catheter. In some embodiments, this limitation is overcome by spiraling the coils 814 around a perimeter of the tubular elongate instrument 810, with a first coil spiral 814a tilted slightly relative to a second coil spiral 814b within the wall of the instrument 800, as shown, for example, in the cross-section of FIG. 8B. Such a configuration requires an elongate instrument with a relatively thick sidewall. An alternative embodiment places two coils 824 nominally parallel in the elongate instrument 820 to achieve the 6-DOF measurement, as shown in FIG. 8C. In some embodiments, the coils 824 are positioned diametrically opposite each other across a cross-section of the elongate instrument 820, because changes in the relative position of the coils can be more accurately determined with increased separation. In some embodiments, the coils are positioned off-center (i.e., less than 180 degrees away from each other) due to the design of the elongate instrument. For example, in FIG. 8D, the placement of the central lumen 832 and pullwires 833 in the elongate instrument 830 creates a non-uniformly thick sidewall 831, limiting placement of the coils 834 to thicker portions of the sidewall. In some embodiments, such as in FIG. 8C, the coils 824 are parallel in both their orientation (e.g., axial alignment) and their position along the length of the elongate instrument 820. With two parallel coils, combined sensor measurement and specifically the roll direction can be calculated by taking the difference in position between the two coil measurements. In some embodiments, the coils 844 may not be placed perfectly parallel along the length of the elongate instrument due to manufacturing tolerances, as shown, for example, in FIG. 8E.

Figure 8E:
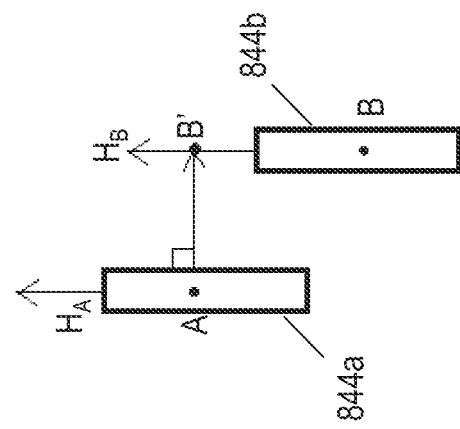

In some embodiments, the math to generate the 6-DOF measurement includes the following, with reference made to FIG. 8E. First, a primary sensor 844a is used to find the point B', which is axially in line with a secondary sensor 844b and directly perpendicular to the orientation of the primary sensor 844a. The vector from A to B' defines the roll direction of the sensor coordinate frame. A position of the "combined sensor" can be computed as the midpoint of vector A→B' if the sensors are embedded in diametrically opposing locations of the instrument wall. If the sensors are not centered around the instrument shaft, as in FIG. 8D, the relationship between the two sensors may be taken into consideration to adjust the position of the combined sensor. In some embodiments, the heading orientation of the combined sensor is determined either by taking the heading of the primary sensor ($H_A$) or by averaging $H_A$ with the heading of the secondary sensor ($H_B$).

This method may cause a significant amount of roll error because the EM sensor measurements tend to have some error in their heading direction, and these errors are combined when producing the roll angle. Accordingly, to address this issue, in some embodiments, a low-pass filter is applied on the roll measurements. Elongate instruments in a body lumen generally do not roll very often or very quickly, so use of a low-pass filter does not significantly impact use of the elongate instrument or sensors. The low-pass filter does stabilize any display of sensor data that takes into consideration the roll information. In an alternative embodiment, a hybrid method is used in which both the slight variations in heading between the coils and the difference in position of the coils is used to calculate the roll direction independently and then combined.

Figure 7:
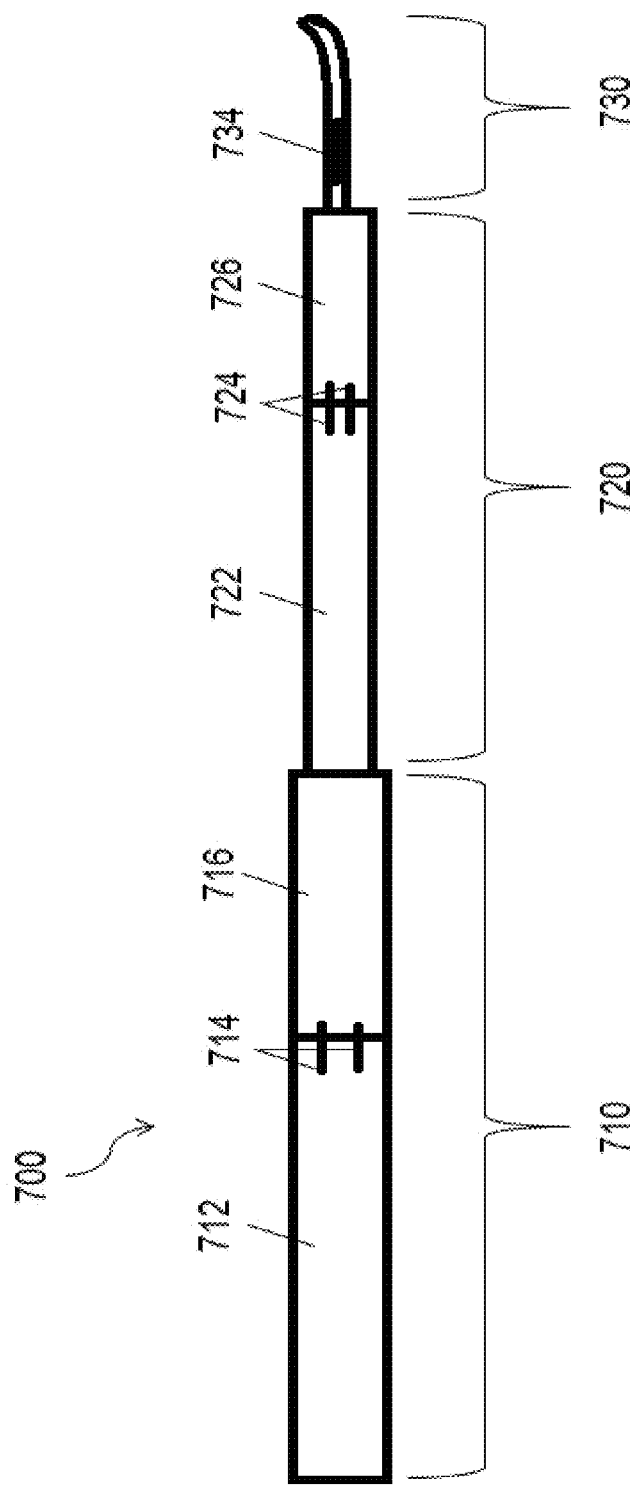
FIG. 7 illustrates a schematic representation of one embodiment of a medical instrument having tracking sensors integrated thereon.

In some catheter embodiments, for example, in FIG. 7, the EM sensor pairs provide position (x, y, z), heading (pitch and yaw), and roll orientation of the sheath and leader articulation sections. The EM sensor pairs may have any of the configurations described with regards to FIGS. 8A-8E, or any other suitable configurations. Additional electromagnetic sensors may be added to different positions within the medical instrument to provide more information on the shape of the instrument.

Registration

Registration is a process that requires relating the reference frame of the sensor FRF to another reference frame of interest. If the positions of two or more objects are known in the same reference frame (i.e., are mapped to the same coordinate system), then the actual positions of each object relative to each other may be ascertained. Thus, with this information, a user can drive or manipulate one of the objects relative to the other objects. In various embodiments, the sensor reference frame FRF is registered to the fluoroscopy reference frame FF or to the fluoroscopic image or anatomical model AMF using a known registration technique. There are many ways this registration can be performed. In some embodiments, the sensor of the medical instrument is measured in relation to the fluoroscopy system frame of reference FF. For example, in some embodiments, a sensing probe is used, which has an EM sensor and a radiopaque marker located in the same physical location on the probe. The sensing probe is placed into the field of view. The 2-D position of the probe is designated by the user in the fluoroscopy field of view (FOV) in images obtained at two different C-arm roll angles. The position of the probe may be designated by the user in three or more different locations. These measurements are then used to sync the sensor location measurements with the selected fluoroscopy locations. In this way, the EM coordinate system is registered to the fluoroscopy coordinate system FF. In most interventional procedures, the reference frame of interest is the visualization frame. The visualization frame is the frame that the user (e.g., a physician) is viewing, and it may include a patient or a live 2-D or 3-D image. The live image may be acquired via fluoroscopy, ultrasound, digital subtraction angiography, live fluoroscopy with a contrast injection into the bloodstream, or other live imaging source. Using such techniques, the goal of registration is to determine the relationship of the frame of reference of the sensor FRF relative to the frame of reference of the patient PRF or to a 2-D or 3-D image or model of the patient.

Virtual Instrument

Various methods of tracking and registering the elongate flexible instrument are described above. In various embodiments, once an anatomical image is acquired, the sensor on the elongate instrument is tracked, and the sensor's frame of reference is registered to the anatomical image's frame of reference, a representation of the elongate instrument is displayed on the anatomical image to facilitate a user's ability to visually track progress of the elongate instrument in the anatomy. The process for displaying the elongate instrument on the image will now be described.

The tracked instrument is simulated by rendering it with 3-D computer graphics and displaying, overlaying, or superimposing it on stored fluoroscopy images. One example of a simulated rendering of an elongate instrument 920 superimposed over the anatomy 910 captured in a stored fluoroscopy image 900 is provided in FIG. 9. This simulated elongate instrument 920 is known as the virtual instrument or the virtual catheter. In some embodiments, the location, orientation, and shape of the virtual instrument 920 are estimated based on commanded data. In some embodiments, sensor measurements are used to improve the quality of the simulation and generate more accurate instrument shapes that are usable in clinical settings. In such embodiments, one or more of the location, orientation, and shape of the virtual instrument 920 is determined with the aid of tracking sensors. The current locations and orientations of the tracking sensors in an anatomical space are known from received sensor measurements. The fixed location and orientation of the sensors in each elongate instrument are also known. From these known data points, a virtual instrument 920 can be drawn that passes through these points. The total lengths and insertion distances of the various components of the elongate instrument are also known. Robotic movements of each component are tracked and this movement can be used to extrapolate the instrument shape between the sensor positions. The rotational orientation of the elongate instrument may also be determined from the sensors as described above to provide an entire 3-D reconstruction of the elongate instrument. One method for displaying the virtual instrument involves using spline curves to interpolate the shape of the elongate instrument between sensors. This method is purely geometric and therefore does not capture the characteristic behavior of a real instrument. Another method involves using a physics-based simulation to model an elongate instrument. In one embodiment, an instrument model comprises a series of points connected such that they maintain realistic positions relative to one another. The virtual instrument seen by the user is rendered as a 3-D object that follows a path through the series of points.

In some embodiments, this virtual instrument information may be displayed to the user to help the user navigate. For example, instinctiveness indicators 930 such as the ring with colored cones shown in FIG. 9 may be added to the virtual instrument 920 and used to signal to the user which direction the instrument will bend when a specific user input command is activated. In the provided embodiment, the directional cones are on opposing sides of the ring (i.e., 180 degrees apart). Directional indicators of any distinguishing colors or shapes may be used. In some such embodiments, corresponding directional indicators may be placed on the user input device. The virtual directional indicators are continuously updated with the position of the elongate instrument to represent the direction the instrument would bend if the corresponding directional indicator on the user input device is activated. For example, in one embodiment, a ring is provided around the virtual instrument 920 with an orange cone and an opposing purple cone. On the user input device, a left button or left side of the joystick may be marked with the orange mark. Activation in this direction would bend the elongate instrument in the direction of the orange indicator on screen. On the user input device, a right button or right side of the joystick may be marked with the purple mark, and activation in this direction would bend the elongate instrument 180° from the first direction. Such an embodiment provides for more instinctive driving than simple "right" and "left" activation buttons, because the elongate instrument may rotate as it is advanced through the anatomy and the viewing angle of the C-arm may also rotate so it cannot be assured that bending the instrument to the left with the input device would result in the instrument bending to the left in the viewing plane. The presence of the 6-DOF position tracking sensors in the tip of the instrument may be used to communicate the actual roll orientation of the instrument tip in the given viewing plane. In some embodiments of robotic assisted driving (described in more detail below), the colored cones on the ring (or other instinctiveness indicators) are augmented to include another shape or other indicator to indicate which direction the system recommends that the instrument be articulated to aim towards the target.

In simulating telescoping catheters using a physics model, it is often advantageous to treat multiple catheters as a single elongated object as it requires less computation. However, this model does not accurately capture the interaction between the catheters, introducing unrealistic constraints in the simulation. For example, the model would be subject to a large amount of torque if it were to match sensor measurements exactly, because real catheters have room to slightly roll relative to each other. This often leads to instability in simulation. In order to resolve the issue, in some embodiments, the model may use only a subset of sensor measurements to reduce the risk of over constraining the model. For example, the roll measurement at the instrument tip may not be rigidly enforced.

In another embodiment, the accuracy of the virtual instrument 920 may be improved by tracking the elongate instrument via computer vision in a fluoroscopy image. Computer vision techniques to track catheters have been described, for example, in US Publ. No. US2016/0228032, the disclosure of which is herein incorporated by reference. The similarity of the fluoroscopic instrument and the virtual instrument can be used to generate bias forces to move the physics model closer to the real instrument shape. In another embodiment, fiber optic shape sensing sensors may be used to estimate the shape of the virtual instrument. In a further embodiment, the commanded robotic instrument insertion length or the commanded angle and heading orientation of an instrument may be tracked and compared to measured instrument position and heading based on sensor data and the delta may be used to update the physics model accordingly.

In some embodiments, a 3-D model of the anatomy is generated from pre-operative imaging, such as from a pre-op CT scan, and the instrument model interacts with the anatomy model to simulate instrument shape during a procedure. For example, in one embodiment, the intersection of the instrument shape with the geometric model of the anatomy produces forces that are included in the simulation of the instrument. In addition, the time history of sensor locations provides insight as to the shape of the anatomy or the possible shape of the instrument. As an instrument passes through blood vessels, the instrument will often straighten or deform the anatomical shape. By tracking the path of the instrument through the anatomy over time, the relative shape of the deformed vessels may be determined and both the instrument model and the anatomical model may be updated.

Interpolated instrument shapes become less accurate in parts of the instrument far away from sensors. When the virtual instrument shape deviates from the actual shape, physicians may inadvertently act on the incorrect information. Therefore, in some embodiments presented herein, a measure of confidence is displayed for each section of the virtual instrument shape so that physicians can make informed decisions. This measurement of confidence is guided by a few principles: the closer to a sensor, the higher the confidence; the higher the curvature between sensors, the lower the confidence; the greater the difference between the known and measured sensor-to-sensor distance, the lower the confidence; and the greater the difference in sensor orientations, the lower the confidence.

In some embodiments, the confidence measure in part of the virtual instrument is shown non-numerically. For example, in one embodiment, the degree of transparency in the virtual instrument 920 corresponds to the measure of confidence. Part of the instrument may be made fully transparent if the confidence is sufficiently low so that the questionable portion of the instrument is hidden from the user. Alternatively, low-confidence may be represented by changing the color or texture of a part of the instrument or by adding animation, such as flashing or scrolling texture. In another embodiment, a flashing icon, such as a radiation icon, may be displayed beside the fluoroscopy image to urge the use of fluoroscopy when the confidence falls below a threshold value. It may start flashing when confidence drops as a way of suggesting that the user use fluoroscopy to acquire an updated image of the anatomy and the instrument. Low-confidence portions of the virtual instrument may flash in time with the radiation icon to better associate low confidence with the need for fluoroscopy.

Virtual Biplane

In various embodiments provided herein, a visualization mode called a "virtual biplane" is provided. In a virtual biplane, the virtual instrument is overlaid on the standard primary image and also on a secondary reference view. The concept of a virtual biplane is introduced in US Publ. No. 2015/0223902 to Walker et al., the disclosure of which is herein incorporated by reference in its entirety. Displaying a representation of the instrument updated in real-time, overlaid on two different views of the anatomy is analogous to what a user would see in a biplane fluoroscopy system. However, as contemplated herein, the biplane view is not an actual live biplane view, but rather, a simulation of the sensed instrument superimposed on the anatomical images. Therefore, it is known as a virtual biplane mode. The catheter or instrument that is displayed, overlaid, or superimposed on the anatomical image is referred to as the "virtual instrument" or "virtual catheter" as described above. In the virtual biplane, the virtual instrument is depicted in two different views of the anatomical background. In some embodiments, both provided views utilize fluoroscopy. In some embodiments, the virtual biplane includes a first fluoroscopic view with an image of the sensed medical instrument overlaid or superimposed on top of the fluoroscopic view. This may be a live fluoroscopic view or a previously acquired fluoroscopic view. The commercially available fluoroscopic systems have the capability of acquiring and storing images. These images may then be displayed as reference images at any point during the procedure. The virtual biplane embodiment presented here also includes a second view, which may be a reference view, for example, a previously-acquired view obtained via fluoroscopy at a different angulation of the C-arm.

In one embodiment, the first and second view may be shown at different magnifications. For example, the first view may show an image at a lower magnification so that more of the instrument and anatomy is seen to help the user understand the global position in the patient whereas the second view may be a zoomed in or magnified view of an area of interest, usually in a different projection from the first view.

As the medical instrument is moved or manipulated through the patient, the tracking sensor in the instrument tracks its movement and the virtual instrument is updated in both views. This provides live 3D tracking of the instrument displayed against images of the anatomy. The position sensor information is registered to each image so that as the image changes (for example, due to a movement in the C-arm), the system can calculate where the sensor measurements line up with the updated image. At any point during the procedure, the user may change the anatomical images used for the virtual biplane. For example, if a physician is attempting to target a first vessel pointing directly anteriorly (i.e., toward the front of the patient), a lateral fluoroscopic projection might be preferred for at least one of the views so that the vessel is perpendicular to the viewing plane, whereas if a second vessel is pointing partly anterior but partly to the side of the patient, than the physician may wish to change over to a more oblique fluoroscopic projection.

A problem with said overlays is that the reference image shows the vessel anatomy at a specific instant in time. If the physician introduces a very inflexible or rigid instrument, the anatomy is deformed, and if the patient moves on the table, the overlay is no longer aligned. If said deformation or misalignment is not corrected in the overlaid reference image, an imprecision or a discrepancy arises when the reference image is superimposed. This can lead to uncertainties in navigation during an intervention in which the overlay serves as a navigation aid. Therefore, in various embodiments, the physician is provided with the option of refreshing the image by taking another live image at any point during the procedure.

In some embodiments, the images are acquired using a C-arm fluoroscope, with one viewing angle acquired prior to the procedure and the other viewing angle acquired intra-procedurally. In some embodiments, both views are displayed simultaneously, for example, adjacent to each other. In other embodiments, one or more of the images are generated by an imaging system that overlays a registered pre-operative or intra-operative 3-D image (e.g., 3-D rotational angiography or cone beam CT) on a live image. In still other embodiments, a pre-operative or intra-operative 3-D image is acquired and displayed, which is not registered or overlaid onto live imaging.

Figure 10A:
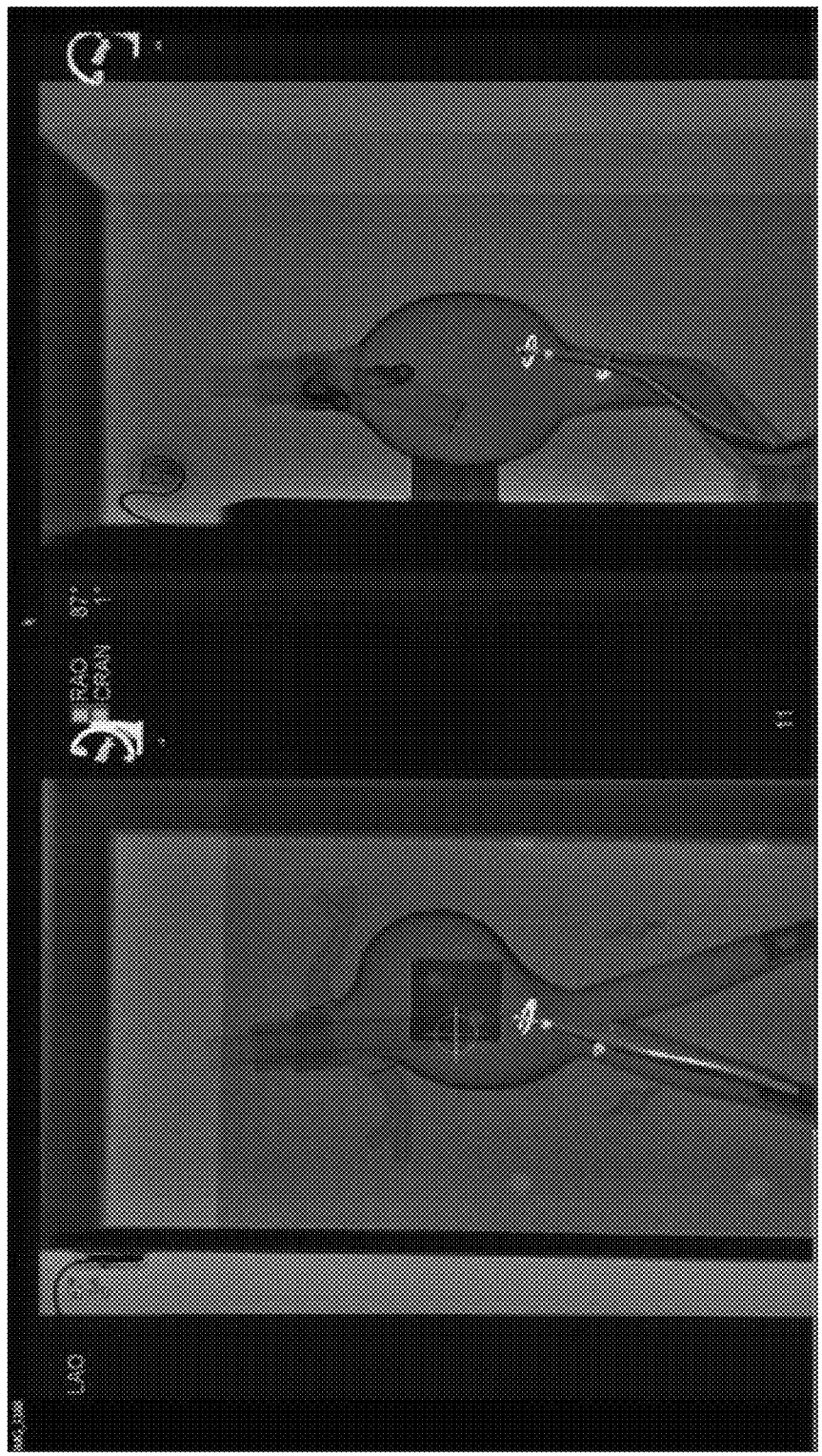
FIGS. 10A-10D each illustrates a screen capture from the visual display of one embodiment of a robot-assisted instrument driving system.
Figure 10B:
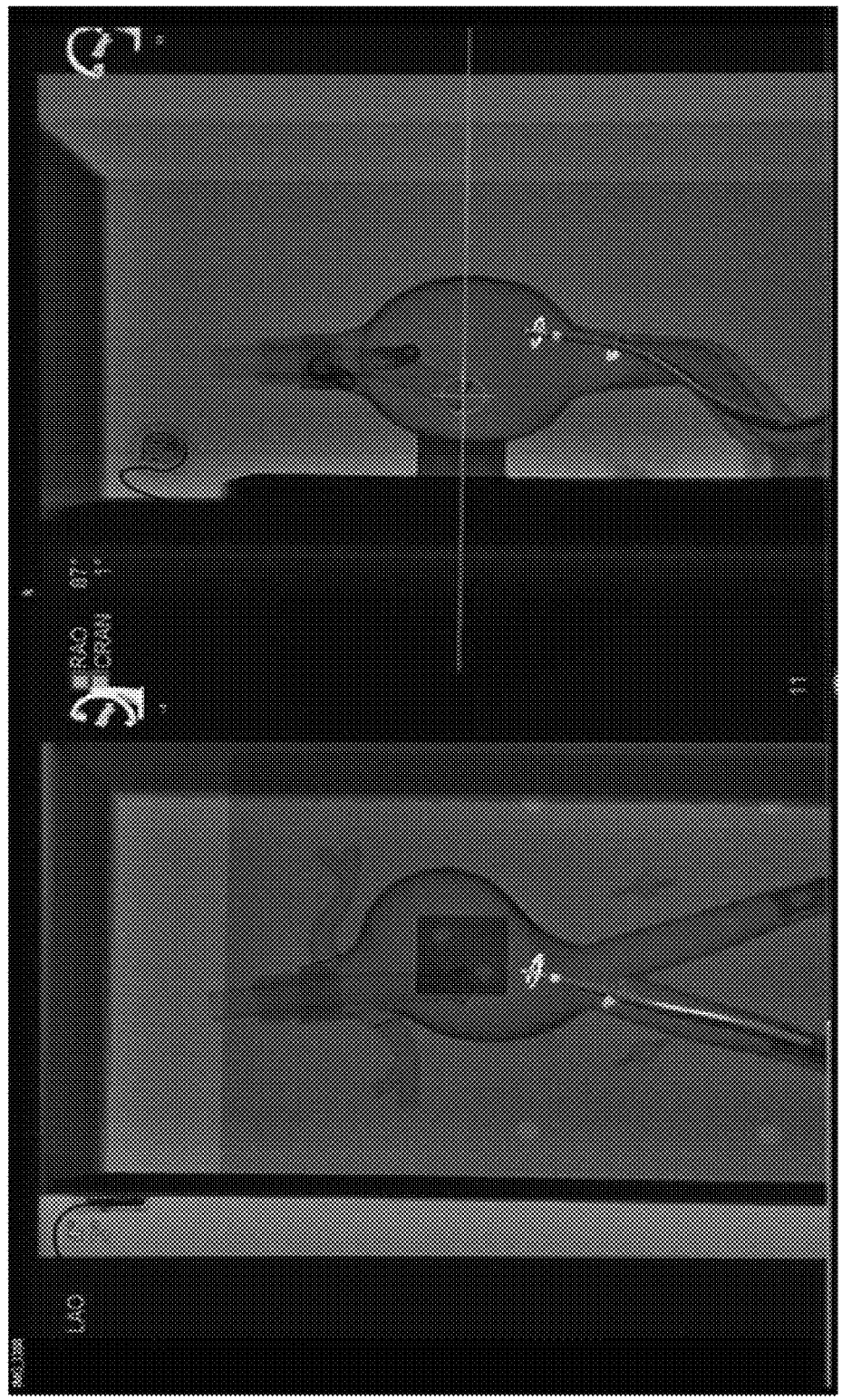
Figure 10C:

An example of a virtual biplane is provided in FIGS. 10A-10C. In some embodiments, two views are displayed on a split screen. In other embodiments, two display screens are provided, each displaying a different view. In the example images captured in FIGS. 10A-10C, the left view directly corresponds to the C-arm angle. If the C-arm is rotated, then this view, including the depicted EM sensing information will change; as the C-arm moves, the EM indicators and virtual instrument will update according to that new C-arm angle. In some embodiments, if the user steps on the fluoro pedal of a fluoroscopic imaging subsystem, the image directly related to the C-arm angle will update based on the live fluoro image. In some such embodiments, if the user releases the fluoro pedal, the last image will be used as a reference image when driving an EM sensed instrument. In such embodiments, the fluoro image may get out of sync with the EM sensor data if the C-arm is rotated but the user is not stepping on fluoro. In such embodiments, a visual indicator may be presented to the user to indicate that the fluoro image is no longer relevant. For example, in some embodiments, the outdated fluoro image may be blackened or given a hue or color or icon to show that it is old information. In other embodiments, a sequence of fluoro images at different angles can be acquired and stored, possibly using a predefined C-arm motion to acquire them, and the reference image can be updated based on C-arm motion even when the user is not stepping on fluoro.

In some embodiments of the virtual biplane, the second image is always a stored image associated with a particular angulation of the C-arm. The particular C-arm angulation is provided and used to allow the sensed instrument information to update live according to that stored view. In the embodiment of FIGS. 10A-10C, the right image is the stored reference image. The stored reference image is a fixed snapshot of a fluoro image taken sometime in the past, which corresponds to the particular C-arm angle. The user can use this stored background image as a reference or roadmap as they are driving. Different visual indicators may be used to show that this is a stored image, such as colors, hues, or icons. At any time, a button or other user input device can be selected to store the live image and C-arm angulation for use as the stored reference in the future.

In some embodiments, it is possible to store multiple reference images each associated with a different respective C-arm angulation. A user or the system may be able to select between the multiple reference images and use different ones at different times without using additional radiation. For example, in some embodiments, the stored image consists of a sequence of images at different C-arm angles. In such embodiments, the sequence of images may be sequentially displayed as the C-arm moves even if the imaging is not live. Alternatively, in such embodiments, the displayed image selected from the sequence of images at different C-arm angles may be chosen by the user through a user interface that allows the user to modify the viewing angle of the second image. In other embodiments, the second image may automatically change to display images from various C-arm angles in a cyclic or periodic fashion providing an animation of the live EM information that provides the user with more three-dimensional information about the shape of the medical instrument or anatomy.

In various embodiments, the images stored in the virtual biplane are often views directly from the fluoroscopy system or other imaging system. In some embodiments, it may also be possible to include overlays from the fluoroscopy system or other imaging system. Such a feature may be helpful in certain workflows, for example, when the user wants to do a contrast injection and store the image during a contrast injection or digital subtraction angiography (DSA) to show the anatomy of interest. The fluoro system may also be used to play back a run of fluoro in the image stored during that playback. In some embodiments, this system may also be used to capture a sequence of frames over the respiration cycle or pulse cycle and play back a video as a stored image instead of a static image.

Alternatively, in some embodiments, the virtual biplane may include one or more renderings of the three-dimensional imaging of the anatomy such as a segmented CT or MM image or intraoperative cone beam CT, IVUS, or ultrasound. In some such embodiments, an image of the sensed medical instrument is placed within the three-dimensional rendering of the anatomy based on the registration of the medical instrument to the anatomical model. Multiple different registration methods may be used as described above and in U.S. Pat. No. 9,014,851, the disclosure of which is herein incorporated by reference in its entirety. Such embodiments provide multiple views for the user during navigation of the medical instrument without requiring live imaging. For example, the embodiments of FIGS. 11A-B each shows a cone beam CT outline overlaid on a fluoro image or alone on a black background. Similar imagery can additionally or alternatively be created using imaging gathered preoperatively, such as from a CT or MM. In these and other embodiments, overlaying a representation of the 3-D anatomy (be it an outline, filled solid area, 3-D rendering, or composite of a stored fluoro image with 3-D imagery) on the background allows for the use of the 3-D data for guidance without additional fluoroscopy. This data can be interfaced with the navigation system through either: a data connection between the navigation system and the imaging system, or displaying frame grabbed video directly or composited with other imaging within the system. In other embodiments, two display screens or two portions of the same display screen show, from different perspectives, views of the three-dimensional anatomical model with a simulation of the sensed medical instrument positioned therein. In some embodiments, one of the displayed views is a simulated endoscopic view (also known as an "Endo View"), which provides the perspective of looking along the instrument or from the front of the instrument within the three-dimensional model of the anatomy. These or other views may supplement or form some of or all the virtual biplane.

Selection of Targets

As described elsewhere herein, an object of the present disclosure is to provide systems and methods for robotic assisted driving of a medical instrument to a target within an anatomical space. In addition to acquiring images of the anatomical space, sensing and tracking the medical instrument, registering the coordinate system (i.e., reference frame) of the medical instrument to the coordinate system of the images, and overlaying a representation of the medical instrument on the images, various methods of robotically assisted driving also require identification of the target. Together, the sensed information of the medical instrument and the identified location of a target can be combined to provide robotically-assisted driving modes. Various modes and embodiments of identifying the target are discussed in more detail below.

In the provided discussion, "targets" are referred to in a generic sense and may refer to a target position, a heading, an ostium shape, or other element or elements of interest to navigation. The target is generally the 3-D center of an anatomical feature that the user would like to access, such as the ostium of a blood vessel coming off the aorta. While a blood vessel is frequently mentioned herein, a target could also correspond to a feature of an implanted device such as an aorta aneurysm endograft or a fenestrated graft. In some embodiments, a target may refer to an anatomical feature such as an ablation site, the annulus of a coronary valve, a suspect nodule or a tumor and may be within any lumen of the body including the airway, gastrointestinal tract, or other lumen or within any organ accessed via a body lumen. When no additional context is provided, "target" in this discussion refers to the three-dimensional position at the center of the entrance of the feature to or through which the user wants to navigate.

In various embodiments, a target is designated in three-dimensional space via one or more user selections of the target position on multiple imaging views. In some embodiments, selection (i.e., designation) of the targets involves a user interaction telling the system where the targets are and how they are oriented. In other embodiments, the system automatically calculates where the targets would be based on known information such as a three-dimensional CT or other target locations, or a combination of both. The three-dimensional imagery may be acquired from a preoperative CT or via imaging during the procedure, such as via cone beam CT. The user may designate the target within an image using a variety of user input devices such as a mouse, trackball, buttons, joystick, or touchscreen. In some embodiments, the user manipulates a user input device to navigate a pointing device icon to the target in the displayed images. The user may further manipulate a user input device (for example, with a button push, mouse click, or finger tap) to select the target. In one embodiment, a trackball and buttons are used by the user to designate targets of interest. In other embodiments, other interfaces are utilized that also provide a means to identify and select points in the images, such as, but not limited to, a computer mouse, touchscreen, gesture device such as Xbox Kinect, joystick, etc. In some such embodiments, an interface allows the user to designate a position on a three-dimensional CT or other three-dimensional image and the system computes the target position, heading, ostium shape, vessel centerline, or other information useful for navigation. This interface may be at an operator workstation or may be positioned bedside or in any convenient location and may be designed to operate in a sterile or non-sterile environment based on the location chosen. In some embodiments, there may be multiple operator interfaces so that, for example, an assistant can choose the target locations at a remote workstation and the physician can continue the navigation bedside.

In other embodiments, the imagery video from an imaging system, as shown for example in FIG. 11B, may be frame grabbed by the system and then processed using computer vision techniques to determine anatomical features of interest to create targets or provide additional guidance as the user is creating the targets. For example, the system may detect body lumen edges based on pixel density and automatically compute the diameters and centerlines of the lumens within the two views; such a system may then allow the user to designate a single point in one image to identify the target position, heading, and ostium size using the anatomical data reconstructed from the imagery.

In addition to the position of the target, it is useful to know the direction or orientation of the lumen beyond the entrance or ostium (i.e., distal to the target). This direction, or "heading", can help the robotically-assisted instrument driving system identify the best approach to enter the lumen. When a user needs to navigate through a target, it is more complex than when a user needs to navigate to a target. Navigation to a target often does not require a specific angle of approach whereas navigation through a target often requires the medical instrument to be lined up squarely with the target before advancing through it. It is easier to enter a lumen if axially aligned with the heading of the lumen rather than positioned perpendicular to it. Therefore, navigation through a target requires an understanding of the anatomy distal to the target and so requires more information, usually at least a second point. In some embodiments, the heading is a single vector direction; in other embodiments, the heading may be a designated or computed lumen centerline. In some embodiments, the user designates a position on the 3-D image and the imaging system computes the shape and orientation of the target opening or the direction of the target lumen based on the 3-D geometry.

In other embodiments, a user is prompted to designate the shape of the lumen entrance so that this entrance can be better shown within the user interface. In one embodiment, the target position, heading direction, and radius of the lumen are identified by the user within at least one of the anatomical views and used to create a circle in space centered at the target position and perpendicular to the heading direction. It is also possible to use multiple points on the edge of the ostium or other element of interest to define a more complex shape such as an ellipse or any other closed shape. The user may designate these points on the display screen. Alternatively, multiple points or line segments may be sufficient to designate and define the shape of a vessel entrance. One embodiment of selecting the target is shown in FIGS. 10A-10C. In the depicted example, a user is shown in FIG. 10A selecting a target in a first image. The user may manipulate a user input device to navigate a set of crosshairs over the target. The user may also be able to manipulate the user input device to change the size of the crosshairs so as to approximate the size of the target. As shown in FIG. 10B, once the target is selected in the first image, the system may determine a plane along which target is located, and a line projection may appear in the second image depicting the plane to facilitate target selection for the user. The user is shown in FIG. 10B moving the crosshairs along the line projection and selecting the location of the target in the second image. As shown in FIG. 10C, following user identification of the target, the target (or a perimeter of the target) remains illuminated to facilitate visualization of the target during instrument navigation. Instrument navigation is then depicted in FIG. 10D.

It is also possible to designate more than one target position (or heading or shape). As one example, different target positions are typically required for the inner and outer members of a medical instrument. A first target may be designated by a user, and a second target may be calculated based on the location, heading, or shape of the first target. For example, if the user identifies a target for the inner member, the system may automatically compute a separate target for the outer member. In some embodiments, the position of the separate target for the outer member is selected such that when the outer member is aligned with the outer member target, the inner member may be automatically or semi-automatically positioned to align with the inner member target. In some embodiments, the heading of the inner member target relative to the heading of the outer member tip or other part of the virtual instrument may be used to determine the distance of the outer member target from the inner member target. In some embodiments, the system takes into consideration the known articulation length of the inner member to determine the outer member target position or heading. In some embodiments, anatomical information from 3-D imaging, such as a pre-op CT, allows the system to better compute the outer member target by taking into consideration lumen walls when computing the optimal outer member distance from the final target. In some embodiments, 2-D anatomical information from one or more images may be used to determine the position of the outer member target by creating constraints in three-dimensional space from the projection of the 2-D anatomical information. In some embodiments, the user determines the outer member target based on the center line path from the 3-D dataset.

In some embodiments, the system is configured to perform a method to modify the target after it is initially specified. For example, instead of setting a new target, the user may be able to use a mouse or other input device to move an existing target in 2-D or 3-D space. In one embodiment, the input device is used to move the target in a single image to fine tune its location in relation to the image or anatomy during navigation. In other embodiments, the system automatically fine tunes the target location based on other information such as 3-D imaging or other live intraoperative imaging such as IVUS.

Separate targets for both inner and outer members (e.g., the sheath and leader catheters) may be similarly reconstructed in this fashion taking into consideration the anatomical shape. As an example, for a sharp vessel takeoff at an angle greater than 90°, such as the right renal vessel 1504 shown in FIGS. 15A-E, the system may determine the best target for the inner and outer members taking into consideration the angle of approach, the size of the lumen proximal to the target, the takeoff direction of the sharp vessel, and the size of the lumen distal to the target.

In some embodiments, targets may be marked within the 3-D imaging system making use of a registered pre-op CT, cone beam CT, or other imaging system. For example, the ostia of vessels may be marked in a 3-D volume as described in U.S. Pat. No. 9,256,940, the disclosure of which is herein incorporated by reference in its entirety. These marks may be exported directly to a flexible instrument navigation system (e.g., the Magellan® system by Hansen Medical Inc.). In this manner, physicians may use their familiar registration, segmentation, and marking toolset, and the data needed to improve navigation is exported to the navigation system as target or waypoint data.

In one example, a trackball or other user input device is used to designate targets via the following sequence: (a) a pair of clicks, one in each of the two views of a virtual biplane, designate the target position for the inner member; (b) a pair of clicks, one in each of the two views of the virtual biplane, designate the target heading direction for the inner member; (c) one click on the heading line designates an outer member target position; and (d) one click designates the radius of the ostium (or the size of any other target).

In some embodiments, a pair of clicks is required to designate a 3-D position of the target. After the first click on the first view (shown in FIG. 10A), that click (or 2-D position in the screen space) defines a line of possible positions in 3-D space based on the camera projection. As shown in FIG. 10B, that line is shown in the second view to aid in identifying the corresponding position of that feature in the alternate C-arm angulation. Once the two clicks are processed, the lines based on the camera projection are calculated and the closest point between those two lines is used for the 3-D target position.

In other embodiments, when the heading direction of a target or anatomical feature needs to be defined as well as its 3D position, a second point on the target (referred to as the "heading position") is required and it may be designated in much the same way as the target 3-D position. Two clicks of the anatomical feature distal to the target from two different views are processed to find the heading position on the anatomical feature, and the designated heading position is then used with the target position to calculate the heading direction. In some embodiments, a line corresponding to the possible heading is drawn before each point is clicked to help the user understand the possible heading positions. In other embodiments, with a first click, the user input device position is used to calculate the two-dimensional heading in the first image, and with a second click, the user input device position in the second image is used to calculate the three-dimensional heading based on the first two-dimensional heading in the first image.

In some embodiments, the size of the target (e.g., the ostium radius) is calculated by using the closest distance between the line defined by the 2-D clicked point and the target position. Many other interfaces may be used to set the target size or shape. For example, multiple clicks around the edges of a target, as seen within 2-D space, may be used to define a size and shape of the target in one view and to identify the target in the other view. In another embodiment, the target radius is traced, for example, using a mouse or trackball. In another embodiment, the size of the target radius is varied as the user input device is moved up and down or left and right and is shown on the screen with a dotted line until the user appropriately actuates the input device (for example, with a click) to set the target size.

Once the targets are designated, multiple icons can be used to show that the target is designated. For example, in some embodiments, such as shown in FIGS. 10A-D, crosshairs or partial crosshairs may show where the target is, a line from the center of that target may show the heading of the lumen, a circle or other shape corresponding to the perimeter of a target may be highlighted, and/or a radar screen showing the positioning of the target within the radar may be provided. When the user switches the selection between different components of the instrument, for example, between leader and sheath catheters, different targets may be displayed in different places corresponding to the different members.

Robotic Assisted Driving

Once the current location of the medical instrument and the location of the target are known, the robotic driving system can help the user navigate. Various embodiments of advanced driving modes are discussed in more detail below. In some embodiments, the instrument driving system is configured to perform one of the disclosed advanced driving modes. In other embodiments, the instrument driving system is configured to perform some of or all the disclosed advanced driving modes. In such embodiments, the user may select the level of assistance or control the user wishes to hand over to the robotic system. In various embodiments provided herein, the one or more advanced driving modes are encoded for in software saved to memory within the controller 34. The advanced driving modes are referred to herein as "robotic assisted driving" or "robotic assisted navigation" modes. In various embodiments provided herein, user commands to the instrument driving system can be augmented with additional robot-determined movements to accomplish navigating the medical instrument to or through the target. In some embodiments, it is most desirable to allow the robotic medical system to automatically command the articulation direction and articulation magnitude of the medical instrument to arrive at or travel through the target. In other embodiments, it may be desirable to allow the user to maintain at least some control over these motions while the robot assists. Therefore, there are various degrees of implementation of robotic assisted driving which are presented herein.

In some embodiments, a computer-augmented driving mode is available to the user. When such a mode is selected, the user may control instrument translation (e.g., insertion and retraction), and while translation is occurring, the robotic system may automatically control articulation magnitude and direction (i.e., bend and roll) and provide additional movements of the instrument tip to help track the instrument to the target location. The automatic selection of the optimal articulation amount and roll direction by the controller prevents the user from needing to both perceive in three dimensions where the target is in relation to the instrument and determine the amount of bend and articulation needed to aim the instrument in that position in three dimensions. In a sense, the robotic instrument driving system (and specifically, the controller or control algorithm of the robotic system) can assist the user in navigation even if the system does not know how to control all degrees of freedom of the instrument to achieve the user's goal.

In another computer-augmented driving mode or embodiment, the user navigates translation and one of articulation and roll, and the robotic system navigates the other of articulation and roll, as needed, to ensure the user-commanded movements lead the medical instrument to the intended location. The exact amount of help or movement provided by the system may vary depending on the application.

One example of computer-augmented driving is depicted in FIGS. 12A-B. FIG. 12A provides a 2-D representation of an elongate instrument, as it would appear to a user within a first view of a virtual biplane. FIG. 12B provides a 2-D representation of the elongate instrument from a different point of view, for example, as it may appear within a second view of the virtual biplane. In the depicted embodiment, the user's goal is to bend the virtual instrument 1200 (and the corresponding real instrument) towards the target 1210 located at the 9 o'clock position in the second view. As shown in FIG. 12B, in the user's first attempt to navigate towards the target 1210, the user inadvertently commanded articulation of the instrument towards 10 o'clock. In some such embodiments of augmented driving, as the user commands roll or rotation of the instrument to find the target 1210, the system automatically updates the mapping of the rotation input from the user to the desired rotation and automatically rotates the instrument tip from the 10 o'clock position to the 9 o'clock position. Alternatively, rather than mapping a user input to the desired motion, the robotic system may augment the user inputs with additional motions to accomplish the tasks. For example, with the target 1210 designated at the 9 o'clock position, when the user commands articulation of the instrument, the robotic system automatically supplements the commanded articulation with a roll command to achieve the desired motion or navigate toward the target.

Robotic assisted driving has been explained above as helping or augmenting user commands. Robotic assisted driving may also include identifying or automatically choosing movements such as the heading direction of the instrument. The controller 34 may use the position and/or heading of the instrument's articulation section and the location, shape, and/or heading of the target to automatically choose the preferred roll plane and articulation magnitude, for example, in order to reach the target or cannulate a target vessel most effectively. As discussed above, the exact implementation may vary based on the application and the user commands. For example, if the user is commanding a roll motion as in FIG. 12B, then the automatic choosing of the preferred roll plane involves mapping the user input to a desired motion or adding additional robot-commanded movements to the user-commanded movements to direct the instrument tip towards the target. If the user is commanding an insertion motion, then the automatic choosing of the preferred roll plane includes augmenting the insertion motion with rotational movement to direct the instrument tip towards the target. Likewise, the automatic choosing of a preferred articulation magnitude may consist of mapping an articulation user-input command to a robot-determined desired articulation movement to thereby direct the instrument tip towards the target when the user commands articulation. Additionally or alternatively, robotic assisted driving may include supplementing an insertion motion with appropriate robot-determined articulation movements to direct the instrument tip towards the target.

Additionally or alternatively, in some embodiments of robot assisted driving, the controller 34 commands the system to display a recommended path or shape of the instrument to the user. One example is provided in FIG. 13. As depicted, the recommended path 1310 through the anatomy 1300 may be denoted with a hidden or dashed line or other suitable marking. The recommended path 1310 depicts an optimal or suitable path within the anatomical image for getting the virtual instrument 1320 from its current position to the target. Such a display allows the user to see how the instrument should be oriented. In some embodiments, the user can then control the instrument, using the path 1310 as a guide. In some such embodiments, the controller 34 is configured to suspend movement of the instrument and notify the user automatically if the instrument deviates from the recommended path. In another embodiment, the system may automatically reduce the insertion speed if the instrument has deviated from the path 1310 or if articulation has not yet reached a desired amount in order to minimize force on the anatomy. In alternative embodiments, the controller 34 may ensure that the instrument follows the recommended path by supplementing or adjusting the user-commanded movements with robot-determined course-correcting movements. In other embodiments, the controller 34 computes one or more insertion, articulation, and/or rotation movements needed to keep the instrument tip on the path 1310. In some embodiments, the controller 34 commands the instrument driver 22 to execute motor actuations needed to implement the one or more movements. In some such embodiments, the controller 34 and the instrument driver 22 work together to drive the instrument along the recommended path 1310 while an auto-pilot feature of the user input device is actuated. In some such embodiments, the user must activate an input device in order to continue progress. At any time, the user may disengage the input device to stop all motion.

The recommended path 1310 may be derived from anatomical information provided by the imaging subsystem. The anatomical information may take the form of a 3-D model of the anatomy, and the recommended path may equal the centerline of a segmented body lumen. In other embodiments, the anatomical information may be in a two-dimensional form such as frame grabbed images from the imaging subsystem. In some embodiments, the anatomical information is used to adjust the computed movements of the instrument as it navigates the anatomy by choosing articulation and roll values that keep the instrument away from the lumen walls. In some embodiments, the anatomical information allows the controller 34 to better determine when to insert one or more members of the instrument to achieve the best shape, maintain a sufficiently large distance away from the lumen wall, and/or enable the instrument to move in the lumen with minimal resistance.

Figure 9:
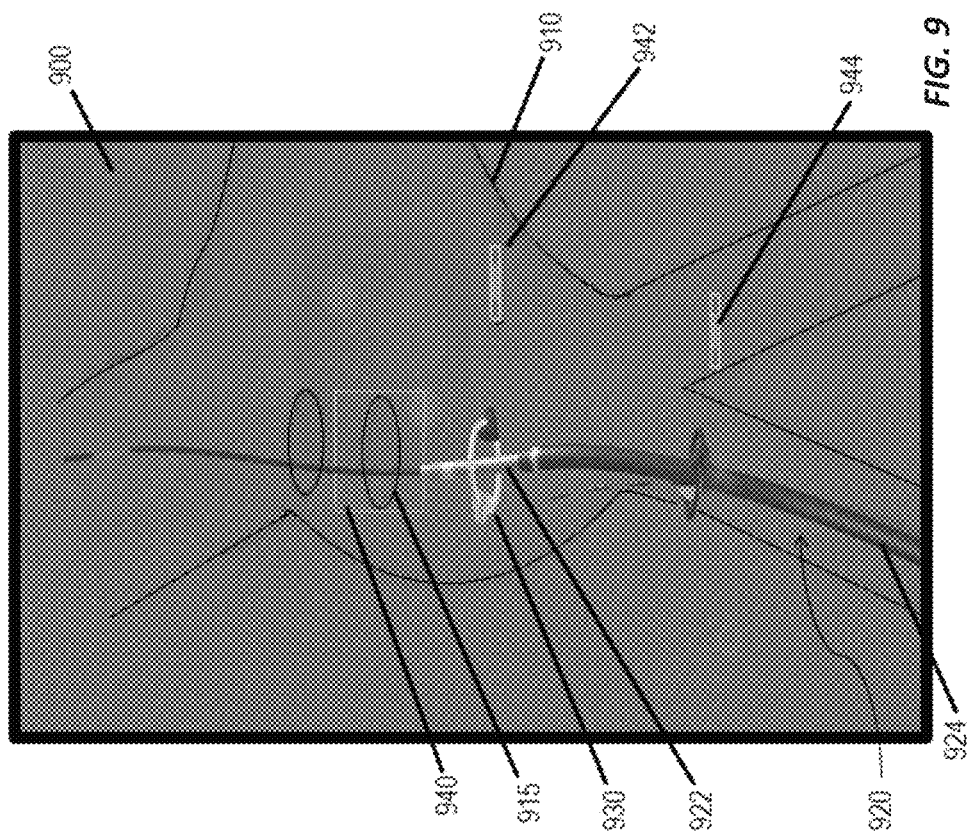
FIG. 9 illustrates a screen capture from the visual display of one embodiment of a robot-assisted instrument driving system.

It can be important to provide feedback to the user to let the user know that the instrument is progressing correctly. In some embodiments, visual indicators are provided to help the user understand the relationship between the instrument and the targets and improve control over the instrument. Visual indicators may be provided to show that the target algorithm is converging on a solution and aiming the instrument towards the target position. In some embodiments, this can be indicated using color on or around the target. For example, in one embodiment, a red border around the target is displayed when the instrument is far from the target, yellow is displayed when nearing the target, and green is displayed when the instrument is aligned with the target. Additionally or alternatively, in some embodiments, convergence on a solution that aims the instrument correctly on the target is depicted with a circle or other shape centered at the target position with a radius equal to the distance of the heading of the instrument from the target position. In other embodiments, such as depicted in FIG. 9, a geometric shape such as a square or circle changes in size to indicate how well the desired path is achieved.

In some embodiments, desirable paths for both the outer member 924 and the inner member 922 of an instrument 920 may be indicated on the screen with lines, dots, geometric shapes, or other imagery. For example, in FIG. 9, the following are depicted: a rectangle 940 around the target 915, a rectangle 942 adjacent the location of the articulation section of the inner member 922, and a rectangle 944 adjacent the location of the articulation section of the outer member 924. In one embodiment, the rectangle 940 around the target 915 changes in color or size to indicate the extent to which the instrument is following a suitable path to the target. In one embodiment, a dot representing a heading direction of each articulation section appears within the rectangles 942, 944 when the articulation sections are in a suitable position in the anatomical space. In some embodiments, such as FIG. 10D, the dot indicates the projection of a distal tip of the instrument onto the plane of the ostium circle or other target plane (similar to a laser targeting system on a rifle placing a dot wherever the rifle is aimed). The dot may be provided to show the relationship between the tip of an articulation section and the target.

Figure 10D:
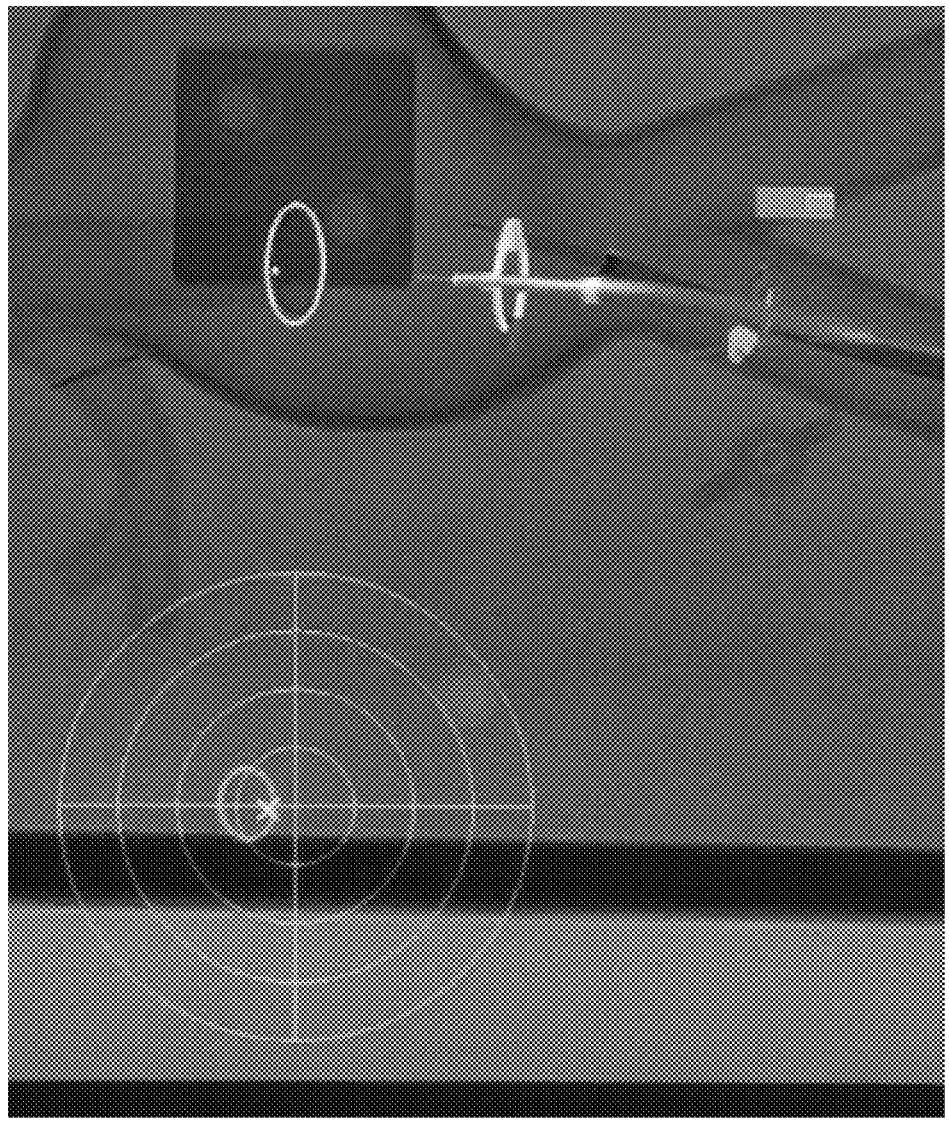

In some embodiments, shown for example in FIG. 10D, a "target radar" is provided as a visual indicator to facilitate understanding of the instrument position relative to the target. In the image, the crosshairs and circles show the space of articulation for the instrument (including articulation magnitude and articulation direction or "roll"). This is similar to polar coordinates. The "x" within the "radar" corresponds to the location of the instrument. Its position relative to the center corresponds to the heading direction and the circle corresponds to the outline of the vessel ostium or other target plane. In such embodiments, when the instrument is rolled, the "x" moves around the circles; when the instrument is articulated more, the x moves toward the outside of the circle, and when the instrument is relaxed, the x moves toward the center. Using this indicator, a user can determine which way to articulate and roll the instrument to align it with the target. A user may also use the targeting radar to discern which direction the instrument is aiming within the target ostium. In a sense, this works as a simplified endoscopic view of the instrument direction and target. Alternatively, a 3-D version of the indicator may be used that draws the indicator in 3-D space; the version may additionally draw the ostium with a projected heading of the instrument on the ostium surface defined by the ostium circle. A user may also use the targeting radar to discern which direction the instrument is aiming within the target ostium. In a sense, this works as a simplified endoscopic view of the instrument direction and target. Alternatively, a 3-D version of the indicator may be used that draws the indicator in 3-D space; the version may additionally draw the ostium with a projected heading of the instrument on the ostium surface defined by the ostium circle.

As also shown, for example, in FIG. 10D, some embodiments may display a shadow instrument representing the position the instrument is expected to assume if a user-entered movement command or the next proposed robot-determined command is implemented. Such an embodiment effectively provides a verification feature and requires another click or other user input before the system proceeds with implementing the commanded movement.

In some embodiments, shown in FIG. 13, dotted lines or other indicators are provided to show the ideal instrument path or the boundary of suitable paths for the instrument, and the user is able to see the difference between the actual instrument shape and the ideal instrument path to identify if deviation is occurring. In some embodiments, once the target is set, the system may allow the user to navigate with limited robotic assistance but will display one or more visual indicators indicating whether the instrument is following a suitable path. Visual cues such as colors, geometric shapes, diagrams, and/or a series of lights (for example, similar to airplane landing lights) may be displayed to show the relationship between the instrument and the target or the recommended path and the current path.

In some embodiments, visual feedback is additionally provided to show when the various advanced driving modes have been enabled for various components of the instrument. For example, when the system is in an inner member driving mode, the target for the inner member may be the only visible target or may be specially highlighted, and similarly, when the system is in an outer member driving mode, the target for the outer member may be the only visible target or may be specially highlighted. In some embodiments, icons to the side of the virtual instrument or lighting on the user input device may indicate when various assisted driving buttons are enabled.

In another embodiment, the system may display an appropriate articulation magnitude and/or direction to the user for the user to follow, in effect, providing textual or graphical turn by turn directions or step-by-step instructions, for example, telling the user which user inputs to select and when. While in such a "Driving Wizard," which may include a sequence of messages (or dialogues or text boxes or symbols) guiding the user towards the target, undesirable motions may also be blocked to ensure that the user drives the instrument correctly or consistently with the guidance. In a similar embodiment, once the target is identified, the system may allow the user to drive, but the controller may create an alert and/or automatically stop movement of the medical instrument if a user command would move the instrument in such a way that reaching the target would become difficult or impossible.

In still another embodiment or driving mode, referred to as robot-controlled navigation, the system fully controls navigation of the medical instrument including one or more of the articulation, roll, and translation. This is considered automated navigation and is made possible once a target position, heading, and lumen size are set. In such a mode, the system may control all movement of the medical instrument once the target is identified; in some embodiments, the system may control all movement while the user is selecting an associated user input command. For example, in some embodiments, the controller may calculate the amount of instrument articulation, rotation, and translation needed to reach the target in an optimal way. The translation, articulation, and rotation may be optimized so that the tip of the instrument is aligned with the target position as well as the target heading. The translation, articulation, and roll may also be optimized so that the shape of the medical instrument does not collide with the anatomy, if the system is able to make use of three dimensional preoperative imaging, other three-dimensional imaging, or two-dimensional imaging showing the outline or projection of the 3-D anatomy. In some embodiments, motion stops when the user stops actuating an automated driving button or other user input device. In other embodiments, it may be possible for the system to drive the instrument automatically even though the user has released the user input device. Some embodiments may automatically alternate between translating the instrument and modifying the articulation of the instrument. Other embodiments may automatically modify the articulation of the instrument as it is translated or allow the combination of user-commanded translation motions with robot-commanded control over articulation and roll. Other embodiments of robotic controlled navigation allow the user to specify the shape of the anatomy in the region so that the system can better calculate the translation, articulation, and/or roll of the instrument to align with the target. Some embodiments may make use of many of these sensing and navigation modalities to automatically compute all articulation and translation of the instrument to achieve a system that is able to navigate the instrument along a prescribed trajectory or a centerline of a body lumen. Methods for extracting the centerline from an image volume are described, for example, in U.S. Pat. No. 9,129,417, the disclosure of which is herein incorporated by reference in its entirety. This centerline generated from the 3-D volume may be used as the target for the automated robotic driving algorithm. In some embodiments, the navigation system may analyze the 3-D data set imported from a pre-op CT, MRI, or cone beam CT directly to compute the sequence of targets in three dimensions. In other embodiments, the navigation system processes one or a small number of 2-D images from an imaging system to improve the targeting algorithms. For example, each single image provides a two-dimensional constraint on the lumen shape when the outline in the 2-D image is projected into three dimensions; such information can be used to inform the target shape, heading, or location. If many images are acquired, such as during a rotation of the C-arm, the navigation system can reconstruct the 3-D shape using 2-D to 3-D reconstruction techniques (similar to how a CT is reconstructed).

Robotic assisted driving techniques may be used to access any anatomical target. One non-limiting example includes the crossing of an occlusion in a blood vessel. In an occluded blood vessel, there is no blood flowing so it is not possible to image the anatomy using an angiogram under fluoroscopy. However, recent developments in CT scanning can identify the thrombus or calcium making up the occlusion and can identify the centerline of the occluded vessel. This three-dimensional information of the centerline of vessels can then be used to generate a sequence of targets that comprise the catheter trajectory. The robotic assisted driving algorithm of some embodiments is configured to use these targets as a path and navigate from the beginning of the occlusion to the location where the vessel reconstitutes by following this centerline while crossing the occlusion. In some embodiments, the robotic control system may automatically extract the centerline data and follow it.

In alternative embodiments, robot-controlled navigation can occur intermittently; for example, a user may begin driving the medical instrument and select the robot-controlled navigation on occasion in order to have the system make path corrections. At times, it is important to prevent the computed articulation or roll from articulating the medical instrument in a constrained situation, because it is important to prevent the instrument from pressing into the anatomy. Similarly, it is important to prevent a computed insertion from inserting the instrument into the anatomy. Some embodiments may include a subsystem that monitors the instrument motion in relation to instrument commands such as articulation and insertion. By modeling the commands and comparing them to the measured catheter shape, the system is able to determine whether it is likely that the medical instrument is contacting the anatomy. Some embodiments may also calculate, based on this difference between the commanded shape and the measured shape, an estimate of the force applied on the instrument by the anatomy (and likewise, the force of the instrument on the anatomy). If the computed force gets large, the system may prevent further motion or cause a relaxation of the instrument to reduce this force on the anatomy. Some embodiments may also provide a message to the user or prevent assisted navigation when the computed force becomes too large. Some embodiments may also compute this force even when the user is not using assisted navigation to prevent the user from inadvertently causing too much force on the anatomy during navigation.

During navigation, the instrument commands are represented as an articulation magnitude, roll angle, and insertion length, and therefore the controller directly modifies the commands to facilitate the driving. The commands are modified to serve different tasks at different stages of driving. For example, in the beginning, the focus may be on cannulating a vessel, and the controller may focus on aiming at the target. As the procedure progresses, and the flexible instrument approaches the target, the controller may focus on bringing the instruments through the target, requiring a different strategy than aiming the instruments at the vessel. In both cases, the modifying commands must be defined in the same coordinate system as the commands issued by the physician. In various embodiments, the desired articulation and roll commands are defined in a frame of reference of the instrument sensors, often located at the base of the articulation section. In some embodiments, the frame of reference may be computed from the virtual instrument shape, which can be defined by a combination of one or more of the sensor data, the articulation command to the medical instrument, a simulation of the instrument dynamics, and a model of instrument behavior. Once the target is also identified in this frame of reference, the desired articulation and roll commands are generated to aim the instrument at the target. In some embodiments, a search algorithm is employed to find the optimal articulation and roll angle. In another embodiment, an optimization procedure can determine the best articulation, roll, and insertion.

In another embodiment, the frame of reference of the instrument is no longer attached to the base of the instrument's articulation section, but is instead calculated based on the shape of the virtual instrument constructed from sensor measurements as well as commands to the instrument. The coordinate frame at the distal tip of the instrument is directly measured by the sensors, but the frame at the base of the articulation section is calculated from inverting the kinematics that describes the relationship between the articulation magnitude and the position of the distal tip. The resulting frame of reference is no longer placed at the base of the articulation section, but instead takes into consideration the shape of the instrument and the command that caused the instrument to take the shape. This may lead to faster convergence and improved targeting performance.

In open loop control, calculations from the sensors are used with the target location data to compute a single direction to move the medical instrument. This approach has the advantage of control stability, but variations in instrument behavior may prevent the instrument from aiming directly at the target. In closed loop control, the system takes into consideration the sensed position of the instrument as it moves and adjusts the instrument command accordingly to make the aim of the instrument converge on the target. In one embodiment, a polar coordinate system such as the targeting radar indicator displayed in FIG. 10D is used to compute the difference between the center of the target and the current heading of the instrument. A change in articulation and roll angles can be identified and added to the current instrument command to better align the instrument with a target. In various embodiments, large commanded changes may need to be divided into a series of smaller steps to prevent overshooting the target. On the other hand, a miniscule change or step may be magnified to overcome non-linear characteristics of the instrument, such as friction, dead-zone, or slack in a pullwire, to ensure that the instrument exhibits noticeable motion during assisted driving. In addition to the setting time, a distance threshold may be implemented to stop further modifications to the command if the aim of the instrument is close enough to the target. The threshold prevents the instrument from unnecessarily overshooting the target and keeps the aim of the instrument from drifting away from the target once the target has been reached. In various embodiments, once a desired instrument articulation and roll are computed, the controller 34 breaks them into driving commands. In one embodiment, the instrument may be commanded to first relax if it needs to change roll direction more than 90 degrees instead of rotating the instrument. Once the instrument is fully relaxed, the roll angle can be set directly so that the instrument bends in the desired roll direction. This is similar to the adaptive catheter control strategies outlined in US Publ. No. 2016/0213884, the disclosure of which is herein incorporated by reference in its entirety.

Robotic assisted driving may involve the task of advancing an instrument formed of a plurality of members towards or through a target. In some embodiments, one or more of the above systems and methods are used to robotically assist driving an inner member through the target. Once the leading, inner member is passed through the target, an enhanced robotic assisted driving algorithm and method may be implemented so that any coaxial outer members "follow" over the leading member. During navigation of the outer member, the shape of the inner member provides an ideal path for the outer member to follow.

In some embodiments, "following" involves inserting the outer member towards the target while articulating the outer member in the direction of the target, thereby following a path similar to the ideal path. In other embodiments, additional steps are needed to ensure accurate following and to avoid prolapse or loss of wire or instrument position. There is a risk of prolapse any time a flexible instrument changes directions during insertion. Prolapse is a situation where insertion of the instrument causes a proximal portion of the instrument to continue moving in the direction of a previous insertion command and bulge away from a target instead of changing directions and advancing with the distal tip toward the target. In FIG. 13, for example, a prolapse in the leader catheter 1324 is shown as a bulge above the level of the target ostium 1302; in this situation, further insertion of the leader catheter 1324 would cause it to buckle further up into the aorta 1304 and ultimately pull the tip of the leader catheter 1324 and the guidewire 1322 out of the ostium. This situation is important to avoid because it can add significant delays to a procedure. The prolapse of the leader catheter 1324 or other inner member is often controlled by the orientation of the sheath catheter 1326 or other outer member. For example, in FIG. 13, the likely cause of the prolapse in the leader catheter 1324 is the fact that the tip of the sheath 1326 is aimed significantly away from the ostium 1302 of the vessel and the change in direction was too great. If the sheath catheter 1326 were instead articulated to point more towards the ostium 1302, the leader catheter 1324 would be directed more towards the target and would have more support as it is inserted. The additional support enables the insertion motion to move the leader catheter 1324 through the ostium 1302 and into the vessel instead of further up into the aorta 1304.

Additionally or alternatively, in some embodiments, avoiding prolapse involves retracting an inner member 1324 before articulating the outer member 1326 towards the bend or target. Because the controller 34 is aware of the shape of the instrument 1320, some embodiments make use of this information to automatically avoid these prolapse situations or, if they are detected, to move the instrument 1320 in such a way that the prolapse is removed. In some embodiments, the controller 34 is programmed and the system configured to detect prolapse within the instrument and notify the user and/or stop motion.

In some embodiments, avoiding prolapse involves relaxing the outer member 1326 articulation then articulating the outer member 1326 in the path direction of the guidewire 1322 or inner member 1324. The path of the guidewire 1322 or inner member 1324 may be defined by the virtual instrument shape generated from the sensor data. The shape of the virtual instrument constructed from the sensor measurements is naturally smooth and closely mimics that of the real instrument. The virtual instrument provides sufficient information to generate proper commands for the real instruments.

In some embodiments, instrument commands may be further refined based on the position and heading of the target as well as the shape of an instrument portion. In one embodiment, the controller 34 determines an appropriate articulation angle $\theta_{cmd}$ for the outer member based, in part, on the shape of the inner member. As shown in FIG. 14, to determine the appropriate articulation angle $\theta_{cmd}$, the average inner member shape in a local area is calculated, and the controller solves for the articulation angle $\theta_{cmd}$ that will make the outer member curvature match the average inner member shape the best. The controller may then command the instrument driver to achieve this articulation angle. For example, in FIG. 14, a first heading value $H_1$ is sampled at a first location $L_1$ proximal to the tip of the outer member 1404, and a second heading value $H_2$ is sampled at a second location $L_2$ distal to the tip of the outer member 1404. The heading values are averaged to find the average shape of the inner member 1402 in the sampled region, denoted as $\theta_{track}$. The length of the articulation section is denoted as d, and the length of the sampled portion (i.e., the length of the inner member 1402 between $L_1$ and $L_2$) is denoted as d'. The appropriate articulation angle $\theta_{cmd}$ is then calculated using the following proportion equation: $\theta_{cmd}=\theta_{track}(d/d')$. In another embodiment, the curvature of the articulation section is determined from averaging the curvature across portions of the virtual instrument.

In various embodiments, the algorithms used to calculate the articulation and roll of an instrument in assisted driving may need to take into consideration the pulsatile flow in the arteries as well as heart and breath motions. In some embodiments, biological motions of the patient may be predicted and used to improve the performance of assisted driving. For example, in the images, the target may appear to move in sync with the patient's motion. Motion of the target may be sensed based on the instrument motion, live imaging such as fluoroscopy, or user input. The systems and methods of some embodiments detect and compensate for this cyclic motion, stabilizing the algorithm to converge faster. Some embodiments use an adjusted or moving target during computations of the translation, articulation, and/or roll.

One embodiment of robotic-assisted driving is provided in FIGS. 15A-15E. In the provided illustrations, a virtual instrument 1510 is superimposed on the anatomical image 1500. The virtual instrument 1510 includes a virtual guidewire 1512, a virtual inner member 1514, and a virtual outer member 1516. In the provided example, the anatomy is representative of a patient's left renal artery branching from the aorta when viewed from an anterior/posterior projection, but similar branches are present in other lumens within the body. The dashed line 1520 is provided in the visual display of some embodiments to show the desired target path of the instrument 1510 from its current position to the user-set target 1530. The dashed line 1520 (i.e., the desired path) may be positioned at the centerline of the body lumen when within a relatively large or straight lumen 1502 and may follow a lowest energy curve or optimal path based on the bending radius of the instrument as it navigates lumen branches 1504.

The end target 1530 for the instrument 1510 is in the side branch vessel 1504. If this target endpoint were established as the first target for both the inner member 1514 and the outer member 1516, then both members would bend towards the target as shown by the solid arrows of FIG. 15A and deviate from the desired path. This would lead to both members colliding with the wall of the aorta 1502. To prevent such an outcome, in various embodiments of robotic-assisted driving, the controller 34 is configured to determine and set one or more intermediate targets that the instrument components aim for along their path to the final user-designated target. For example, as shown in FIG. 15B, in the depicted progression, the controller 34 has set a first target point 1532 at the ostium of the vessel. This is a suitable target point for the inner member 1514 in this configuration but not for the outer member 1516. If the outer member 1516 were bent towards the target 1532, then the inner member 1514 would need to make a very sharp bend as shown by the dashed line 1522. Instead, it is preferred to set up an additional target point for the outer member, as shown by the visual indicator 1534 in FIG. 15C. The target point 1532 for the inner member remains unchanged. Both the target points 1534 and 1532 are located approximately on the preferred trajectory or desired target path 1520 of the instrument. Once the target 1534 for the outer member is set, any movements of the outer member 1516 determined and commanded by the robot will be selected to direct the tip of the outer member 1516 towards the target as shown by the long arrow. Similarly, once the target 1532 is set for the inner member 1514, any movements of the inner member 1514 determined and commanded by the robot will be selected to direct the inner member 1514 towards that target 1532 as shown by the short arrow.

It is worth noting that FIGS. 15A-E depict a single 2D image of the target and the instrument for simplicity. In various embodiments of the surgical environment, a second image of a different projection is also provided. The concepts described here for a single 2D image also hold true in 3D. The inner and outer members are both assigned a target in 3D space and are commanded to move towards those targets.

Figure 15D:
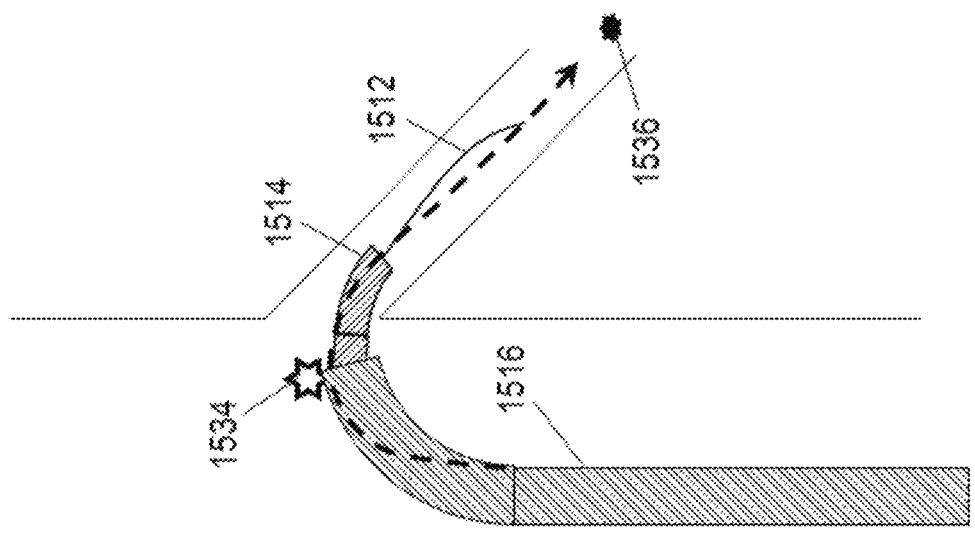
Figure 15C:
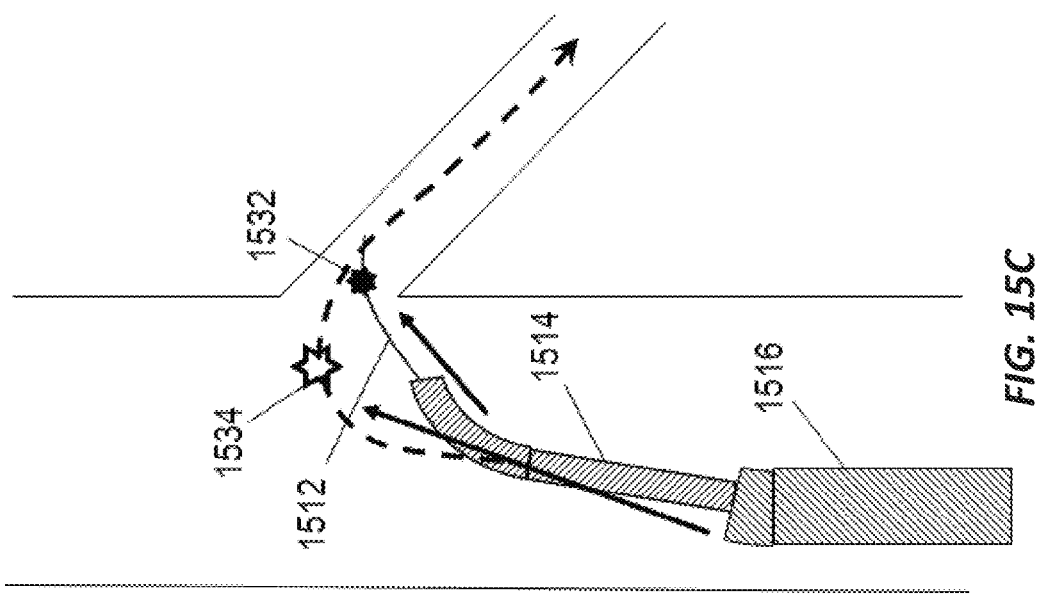

As shown in FIG. 15C, once the inner member 1514 and the outer member 1516 are aligned towards their targets and are close to the targets, the guidewire 1512 may be advanced through the inner member target 1532. Once the guidewire 1512 is advanced through the target 1532, further forward motion of the instrument may be programmed to follow the guidewire. The inner member 1514 may need to be relaxed or straightened as it advances beyond the apex of the bend to follow the guidewire 1512; however, in some embodiments, it may not be necessary to set new targets for the instrument.

Figure 15E:
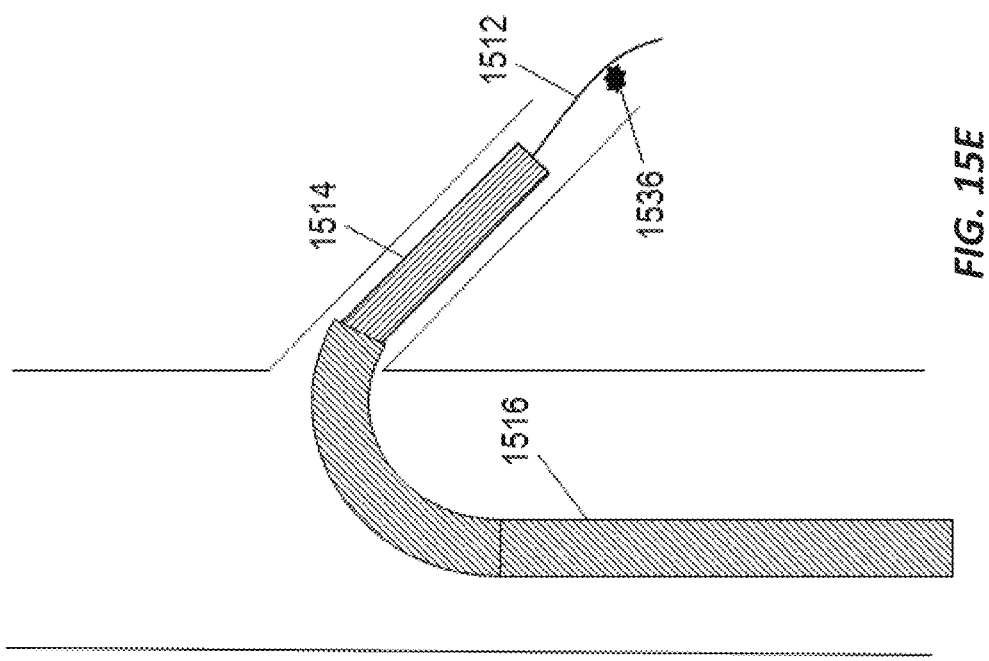

In other embodiments, if further navigation into complex anatomy is required, the inner member target may be relocated, as shown in FIG. 15D. In the illustration, the new target 1536 is set at the distal end of the branch lumen while the outer member target 1534 remains outside the ostium of the vessel so that the outer member 1516 provides adequate support on the desired dashed line. The outer member 1516 eventually is commanded by the controller 34 to "follow" the inner member 1514, as shown in FIG. 15E. As with the inner member 1514, once the outer member 1516 advances beyond its target 1534, the controller 34 may direct the outer member 1516 to follow the inner member 1514 or the guidewire 1512. Alternatively, a new target point may be set for the outer member 1516.

In other embodiments, such as ablation procedures, the control algorithm of the controller 34 may be set up such that the instrument 1510 never advances passed the target. In ablation procedures, the goal is to get a catheter tip to a target and it might be desirable as a safety measure to never allow the catheter or other instrument to extend beyond the target point. This would reduce the risk of inadvertent vessel perforation.

As discussed above, the degree of operator involvement in the setting of the targets and the driving towards or through the targets may vary. In one preferred embodiment, the operator identifies the end target, the robotic system identifies a centerline or lowest energy path, the operator control insertion of the guidewire and insertion and bend of the inner member, and the controller 34 automatically determines and controls the roll of the inner member and all movement (i.e., insertion, bend, and roll) of the outer member.

While multiple embodiments and variations of the many aspects of the invention have been disclosed and described herein, such disclosure is provided for purposes of illustration only. Many combinations and permutations of the disclosed systems and methods are useful in minimally invasive medical intervention and diagnosis, and the systems and methods are configured to be flexible. The foregoing illustrated and described embodiments are susceptible to various modifications and alternative forms, and it should be understood that the invention generally, as well as the specific embodiments described herein, are not limited to the particular forms or methods disclosed, but also cover all modifications, equivalents, and alternatives falling within the scope of the appended claims.

What is claimed is:

1. A method for driving a flexible medical instrument in three dimensional space within an anatomy, the method performed by a robotic medical system and comprising:
    acquiring an anatomical image using an imaging subsystem of the robotic medical system;
    acquiring localization information for the instrument from a tracking sensor integrated in the instrument;
    registering the instrument to the anatomical image;
    overlaying a representation of the instrument on the anatomical image for display to a user;
    identifying a target on the anatomical image;
    receiving a user command to drive the instrument, the user command received from the user via a user input device;
    identifying, based on the localization information of the instrument and the identified target, a pathway suitable for navigating the instrument from its current position towards the target;
    overlaying a representation of the pathway suitable for navigating the instrument from its current position towards the target on the anatomical image for display to the user.

2. The method of claim 1, wherein identifying the suitable movement comprises determining a suitable change in instrument position in at least one degree of freedom.

3. The method of claim 2, further comprising directing the change in instrument position in the at least one degree of freedom.

4. The method of claim 3, wherein the change in instrument position in at least one degree of freedom is repeatedly and automatically identified, directed, and implemented by a controller and a communicatively coupled instrument driver using a closed loop control algorithm as the instrument moves towards the target.

5. The method of claim 1, wherein receiving the user command to drive the instrument comprises receiving one or more user commands to position the instrument in one or more degrees of freedom, and wherein the method further comprises adjusting the instrument in accordance with the user commands and automatically adjusting the instrument in one or more uncommanded degrees of freedom.

6. The method of claim 1, further comprising automatically driving the instrument to the target using the instrument driver.

7. The method of claim 1, wherein receiving the user command comprises receiving a command at the user input device to drive the instrument in a single two-dimensional plane, and wherein identifying the suitable movement comprises identifying a suitable rotation of the instrument in a third dimension.

8. The method of claim 1, further comprising setting a sequence of additional targets to navigate the instrument through a specific path.

9. The method of claim 1, wherein the imaging subsystem is a fluoroscopy system.

10. The method of claim 1, further comprising updating the anatomical image during a medical procedure.

11. The method of claim 1, wherein the tracking subsystem comprises at least one of an electromagnetic tracking system and a fiber optic shape sensing and tracking system.

12. The method of claim 1, wherein the target is selected from a group consisting of: an ostium of a branch vessel, an ablation location, a fenestration of an endograft, a branch of an endograft, and an annulus of a valve.

13. The method of claim 1, wherein the anatomical image comprises an image of vasculature obtained by injection of a contrast agent into the vasculature.

14. The method of claim 1, wherein the anatomical image is derived from a CT or MRI 3-D data set and the target is identified from markers on the CT or MRI 3-D data set.

15. The method of claim 1, wherein identifying the target comprises marking a position, orientation, and size of the target.

16. The method of claim 1, further comprising adding indicators indicative of a roll orientation of the instrument onto the overlay of the instrument on the anatomical image.

17. A method for driving a flexible medical instrument in three dimensional space within an anatomy, the method performed by a robotic medical system and comprising:
    acquiring an anatomical image using an imaging subsystem of the robotic medical system;
    acquiring localization information for the instrument from a tracking sensor integrated in the instrument;
    registering the instrument to the anatomical image;
    overlaying a representation of the instrument on the anatomical image for display to a user;
    identifying a target on the anatomical image;
    receiving a user command to drive the instrument, the user command received from the user via a user input device; and
    identifying, based on the localization information of the instrument and the identified target, a pathway suitable for navigating the instrument from its current position towards the target, wherein the instrument comprises an outer member and an inner member in a telescoping configuration; wherein identifying the suitable pathway comprises identifying a route to the target for the inner member; and wherein the method further comprises navigating a distal tip of the inner member to the target and advancing the outer member over the inner member such that the outer member follows over a path defined by the inner member.

18. The method of claim 17, further comprising setting a separate target for the outer member.

19. A method for driving a flexible medical instrument in three dimensional space within an anatomy, the method performed by a robotic medical system and comprising:
    acquiring an anatomical image using an imaging subsystem of the robotic medical system;
    acquiring localization information for the instrument from a tracking sensor integrated in the instrument;
    registering the instrument to the anatomical image;
    overlaying a representation of the instrument on the anatomical image for display to a user;
    identifying a target on the anatomical image;
    receiving a user command to drive the instrument, the user command received from the user via a user input device; and
    identifying, based on the localization information of the instrument and the identified target, a pathway suitable for navigating the instrument from its current position towards the target, wherein overlaying the representation of the instrument on the anatomical image comprises overlaying the instrument representation on at least two different images to depict the instrument relative to the anatomy at different viewing angles.

20. The method of claim 19, wherein a first of the at least two different images is a live fluoroscopic view and a second of the at least two different images is a stored reference image from a previous projection.

* * * * *